US005804407A

United States Patent [19]
Tamaoki et al.

[11] Patent Number: 5,804,407
[45] Date of Patent: Sep. 8, 1998

[54] METHOD OF EXPRESSING GENES IN MAMMALIAN CELLS

[75] Inventors: Taiki Tamaoki; Hidekazu Nakabayashi, both of Calgary, Canada

[73] Assignee: University Technologies International, Inc., Calgary, Canada

[21] Appl. No.: 148,058

[22] Filed: Nov. 4, 1993

[51] Int. Cl.⁶ ..................................................... C12P 21/05
[52] U.S. Cl. ............................................ 435/69.1; 935/34
[58] Field of Search ............................... 435/69.1, 172.3; 514/44; 935/62, 34

[56] References Cited

U.S. PATENT DOCUMENTS 5,206,153   4/1993   Tamaoki et al. ........................ 435/69.7

FOREIGN PATENT DOCUMENTS 0415731   6/1991   European Pat. Off. .

OTHER PUBLICATIONS

Ledley, Human Gene Therapy 2: 77 (1991).
Friedmann, Cancer Supplement 70: 1810 (1992).
Wen et al, DNA Cell Biol. 10: 525 (1991).
Hodgson, Bio/Technology 13: 222 (1995).
Anderson, W.F. (1984) "Prospects for Human Gene Therapy," Science, 226:401–409.
Behringer et al. (1988) "Dwarf Mice Produced by Genetic Ablation of Growth Hormone–Expressing Cells," Genes. & Develop., 2:453–461.
Breitman et al. (1987) "Genetic Ablation: Targeted Expression of a Toxin Gene Causes Microphthalmia in Transgenic Mice," Science, 238:1563–1565.
Breitman et al. (1990) "Genetic Ablation in Transgenic Mice with an Attenuated Diphtheria Toxin A Gene," Molecular and Cellular Biology, 10:474–479.
Giannini et al. (1984) "The Amino–Acid Sequence of Two Non–Toxic Mutants of Diphtheria Toxin: CRM45 and CRM197," Nucl. Acids Res., 12:4063–4069.
Gibbs et al. (1987) "Structure, Polymorphism, and Novel Repeated DNA Elements Revealed by a Complete Sequence of the Human α–Fetoprotein Gene," Biochemistry, 26:1332–1343.
Goring et al. (1987) "In Situ Detection of β–Galactosidase in Lenses of Transgenic Mice with a γ–Crystallin/lacZ Gene," Science, 235:456–458.
Graham et al. (1973) "A New Technique for the Assay of Infectivity of Human Adenovirus 5 DNA," Virology, 52:456–467.
Hamasaki et al. (1992) "Interaction of Interferon–α with Interleukin–1β or Tumor Necrosis Factor–α on Hepatitis B Virus Enhancer Activity" Biochem. Biophys. Res. Comm., 183:904–909.
Hashimoto et al. (1992) "A New Family of Homeobox Genes Encoding Multiple Homeodomain and Zinc Finger Motifs," Mech. Develop., 39:125–126.

Hatano et al. (1992) "Hepatocyte Growth Factor Down–Regulates the α–Fetoprotein Gene Expression in PLC/PRF/5 Human Hepatoma Cells," Biochemical and Biophysical Research Communications, 189:385–391.
Hayashi et al. (1992) "Identification and Characterization of Two Enhancers of the Human Albumin Gene," The Journal of Biological Chemistry, 267:14580–14585.
Huber et al. (1991) "Retroviral–Mediated Gene Therapy for the Treatment of Hepatocellular Carcinoma: An Innovative Approach for Cancer Therapy," Proc. Natl. Acad. Sci. USA, 88:8039–8043.
Kew, Michael C. (ed.) (1984) "Toward an Understanding of the Etiology of Hepatic Tumors," Goldfarb, Stanley Biologic Mechanisms of Hepatocarcinogenesis, Sherman et al. Hepatitis B Virus and Hepatocellular Carcinoma: Molecular Biology and Mechanistic Considerations, Beasley et al. Hepatocellular Carcinoma and Hepatitis B Virus, Newberne, Paul M. Chemical Carcinogenesis: Mycotoxins and Other Chemicals to Which Humans Are Exposed, Kew et al. Relationship Between Hepatocellular Carcinoma and Cirrhosis, Mays and Christopherson Hepatic Tumors Induced by Sex Steroids, Tamburro, Carlo H. Relationship of Vinyl Monomers and Liver Cancers: Angiosarcoma and Hepatocellular Carcinoma, Foster, James H. Treatment of Metastatic Disease of the Liver: A Skeptic's View, Seminars in Liver Disease, 4:iii–v and 89–179.
Lopata et al. (1984) "High–level Transient Expression of a Chloramphenical Acetyl Transferase Gene by DEAE–Dextran–Mediated DNA Transfection Coupled With a Dimethyl Sulfoxide or Glycerol Shock Treatment," Nucl. Acids Res., 12:5707–5717.
McCormick, D. (1985) "Human Gene Therapy: The First Round," Bio/Technology, 3:689, 691–693.
Mitsuoka et al. (1992) "Inhibitory Effect of Prostaglandin $\Delta^{12}$–PGJ2 on Cell Proliferation and α–Fetoprotein Expression in HuH–7 Human Hepatoma Cells," Prostaglandins, 43:189–197.
Morinaga et al. (1983) "Primary Structures of Human α–Fetoprotein and its mRNA," Proc. Natl. Acad. Sci. USA, 80:4604–4608.
Morinaga et al. (1991) "A Human α–Fetoprotein Enhancer–Binding Protein, ATBF1, Contains Four Homeodomains and Seventeen Zinc Fingers," Mol. Cell. Biol., 11:6041–6049.
Moro et al. (1993) "Monoclonal Antibodies Directed Against a Widespread Oncofetal Antigen: The Alpha–Fetoprotein Receptor," Tumor Biol., 14:116–130.

(List continued on next page.)

Primary Examiner—James Martinell
Attorney, Agent, or Firm—Burns, Doane, Swecker & Mathis L.L.P.

[57] ABSTRACT

The present invention relates to a method of expressing a heterologous gene in mammalian cells and a recombinant DNA construct for use in the method. The invention also relates to a method of specifically killing cells which constitutively express AFP.

4 Claims, 23 Drawing Sheets

OTHER PUBLICATIONS

Nakabayashi et al. (1989) "Transcriptional Regulation of α–Fetoprotein Expression by Dexamethasone in Human Hepatoma Cells," The Journal of Biological Chemistry, 264:266–271.

Nakabayashi et al. (1991) "A Position–Dependent Silencer Plays a Major Role in Repressing α–Fetoprotein Expression in Human Hepatoma," Molecular and Cellular Biology, 11:5885–5893.

Nakabayashi et al. (1992) "Selective Expression of a Toxin Gene Under the Direction of Human α–Fetoprotein Gene Regulatory Sequences in the Human Hepatoma Cells—An Approach to Hepatocellular Carcinoma Gene Therapy," Human Gene Therapy, 3:614 [Abstract].

Nakao et al. (1989) "Involvement of an AFP1–Binding Site in Cell–Specific Transcription of the Pre–S1 Region of the Human Hepatitis B Virus Surface Antigen Gene," Nucleic Acids Research, 17:9833–9842.

Nakao et al. (1990) "c–Ha–ras Down Regulates the α–Fetoprotein Gene but not the Albumin Gene in Human Hepatoma Cells," Mol. Cell. Biol., 10:1461–1469.

Nakao et al. (1991) "Transforming Growth Factor β1 Differentially Regulates α–Fetoprotein and Albumin in HuH–7 Human Hepatoma Cells," Biochemical and Biophysical Research Communiccations, 174:1294–1299.

Nakata et al. (1992) "A Possible Mechanism of Inverse Developmental Regulation of α–Fetoprotein and Albumin Genes," The Journal of Biological Chemistry, 267:1331–1334.

Nerenstone et al. (1988), "Clinical Trials in Primary Hepatocellular Carcinoma: Current Status and Future Directions," Cancer Treatment Reviews, 15:1–31.

Neumann et al. (1982) "Gene Transfer into Mouse Lyoma Cells by Electroporation in High Electric Fields," EMBO J. 1:841–845.

Otsuru et al. (1988) "Analysis of Alpha–Fetoprotein Gene Expression in Hepatocellular Carcinoma and Liver Cirrhosis by in Situ Hybridization," Cancer, 62:1105–1112.

Palmiter et al. (1987) "Cell Lineage Ablation in Transgenic Mice by Cell–Specific Expression of a Toxin Gene, Cell", 50:435–443.

Pappenheimer, A.M. Jr. (1977) "Diphtheria Toxin," Ann. Rev. Biochem., 46:69–94.

Potter et al. (1984) "Enhancer–Dependent Expression of Human K Immunoglobubin Genes Introduced into Mouse Pre–B Lymphocytes by Electroporation," Proc. Natl. Acad. Sci. U.S.A., 81:7161–7165.

Sakai et al. (1985) "The Human α–Fetoprotein Gene: Sequence Organization and the 5' Flanking Region," The Journal of Biological Chemistry, 260:5055–5060.

Sawadaishi et al. (1988) "Interaction of a Hepatome–Specific Nuclear Factor with Transcription–Regulatory Sequences of the Human α–Fetoprotein and Albumin Genes," Molecular and Cellular Biology, 8:5179–5187.

Tamoki, T. (1991) "Alpha–Fetoprotein as a Tumor Marker: Thoughts on the Molecular Mechanism for Controlling the Gene Expression." Kagaku To Seibutsu [Chemistry and Organisms], 29:631–639 (translation).

Tsutsumi et al. (1993) "Regulation of Albumin and α–Fetoprotein Gene Expression by Colloid Osmotic Pressure in Human Hepatoma Cells," Gastroenterology, 104:256–262.

Uchida et al. (1973) "Diphtheria Toxin and Related Proteins I. Isolation and Properties of Mutant Proteins Serologically Related to Diphtheria Toxin," J. Biol. Chem., 248:3838–3844.

Urano et al. (1984) "Tandem Arrangement of the Albumin and α–Fetoprotein Genes in the Human Genome," Gene, 32:255–261.

Urano et al. (1986) "The Human Albumin Gene: Characterization of the 5' and 3' Flanking Regions and the Polymorphic Gene Transcripts," The Journal of Biological Chemistry, 261:3244–3251.

Urano et al. (1991) "Interstitial Chromosomal Deletion within 4q11–q13 in a Human Hepatoma Cell Line," Cancer Res., 51:1460–1464.

Watanabe et al. (1987) "Cell–Specific Enhancer Activity in a Far Upstream Region of the Human α–Fetoprotein Gene," The Journal of Biological Chemistry, 262:4812–4818.

Wong and Neumann (1982) "Electric Field Mediated Gene Transfer," Biochem. Biophys. Res. Comm., 107:584–587.

Wu et al. (1985) "Acetaminophen Hepatotoxicity and Targeted Rescue: A Model for Specific Chemotherapy of Hepatocellular Carcinoma," Hepatology, 5:709–713.

Wu et al. (1987) "Receptor–Mediated in vitro Gene Transformation by a Soluble DNA Carrier System," J. Biol. Chem., 262:4429–4432.

Yamaizumi et al. (1978) "One Molecule of Diphtheria Toxin Fragment A Introduced into a Cell Can Kill the Cell," Cell, 15:245–250.

Yamamoto et al. (1990) "Expression of Human α–Fetoprotein in Yeast," Life Sci., 6:1679–1686.

T. Tamaoki and H. Nakabayashi, "Mechanisms of Regulation of the Human alpha–Fetoprotein Gene", *Recent Progress in Tumor Marker Studies* (H. Okura, ed.), pp. 8–18, Chugai Igaku Co., Tokyo, 1992.

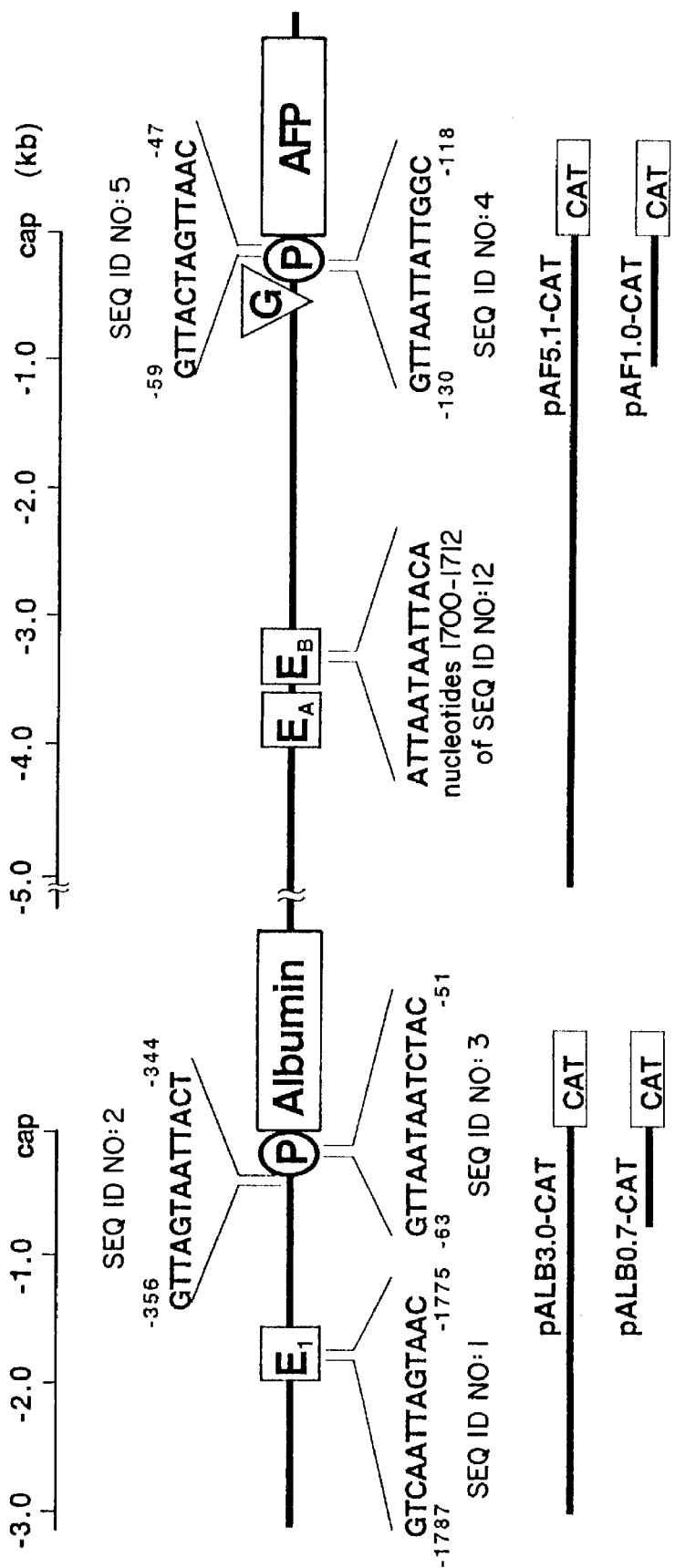
FIG_1A

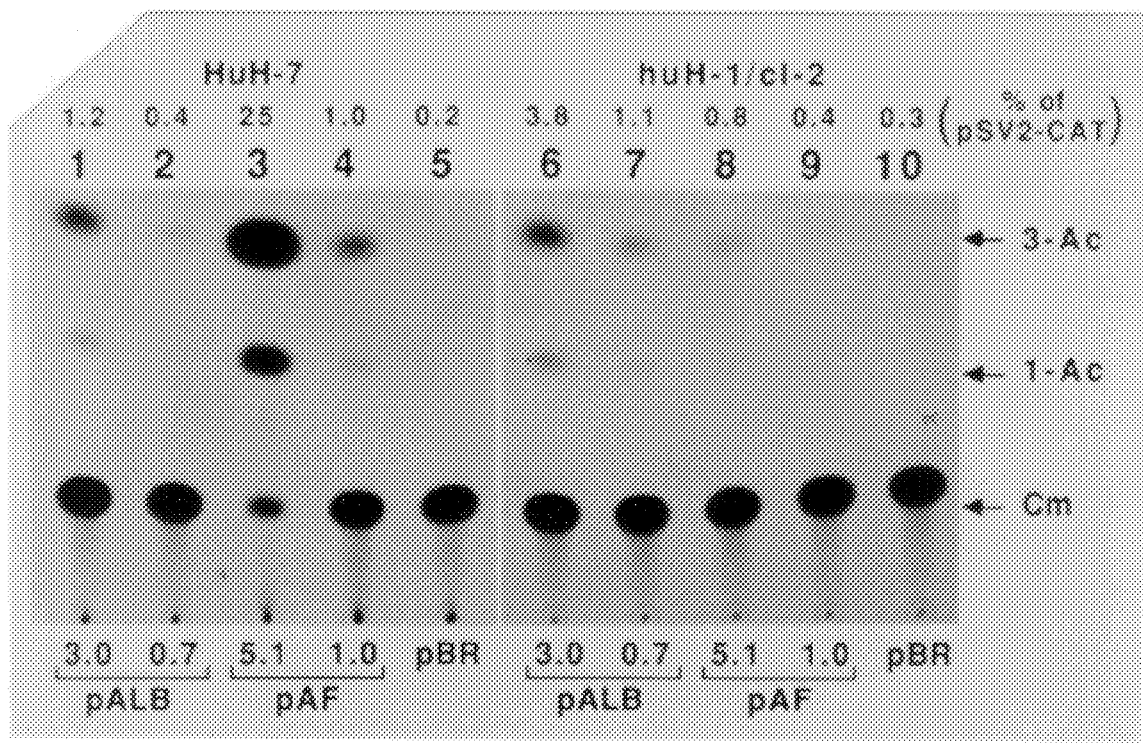
FIG_1B
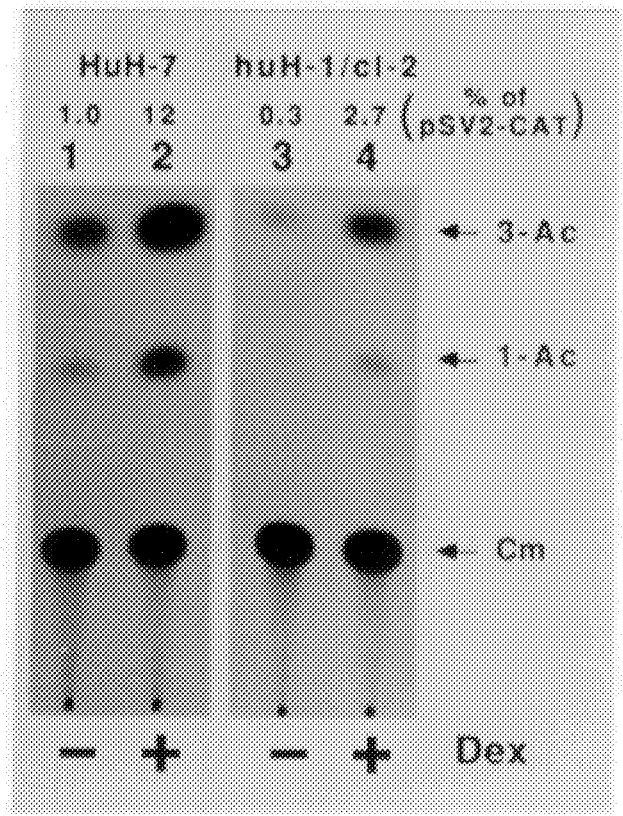
FIG_1C

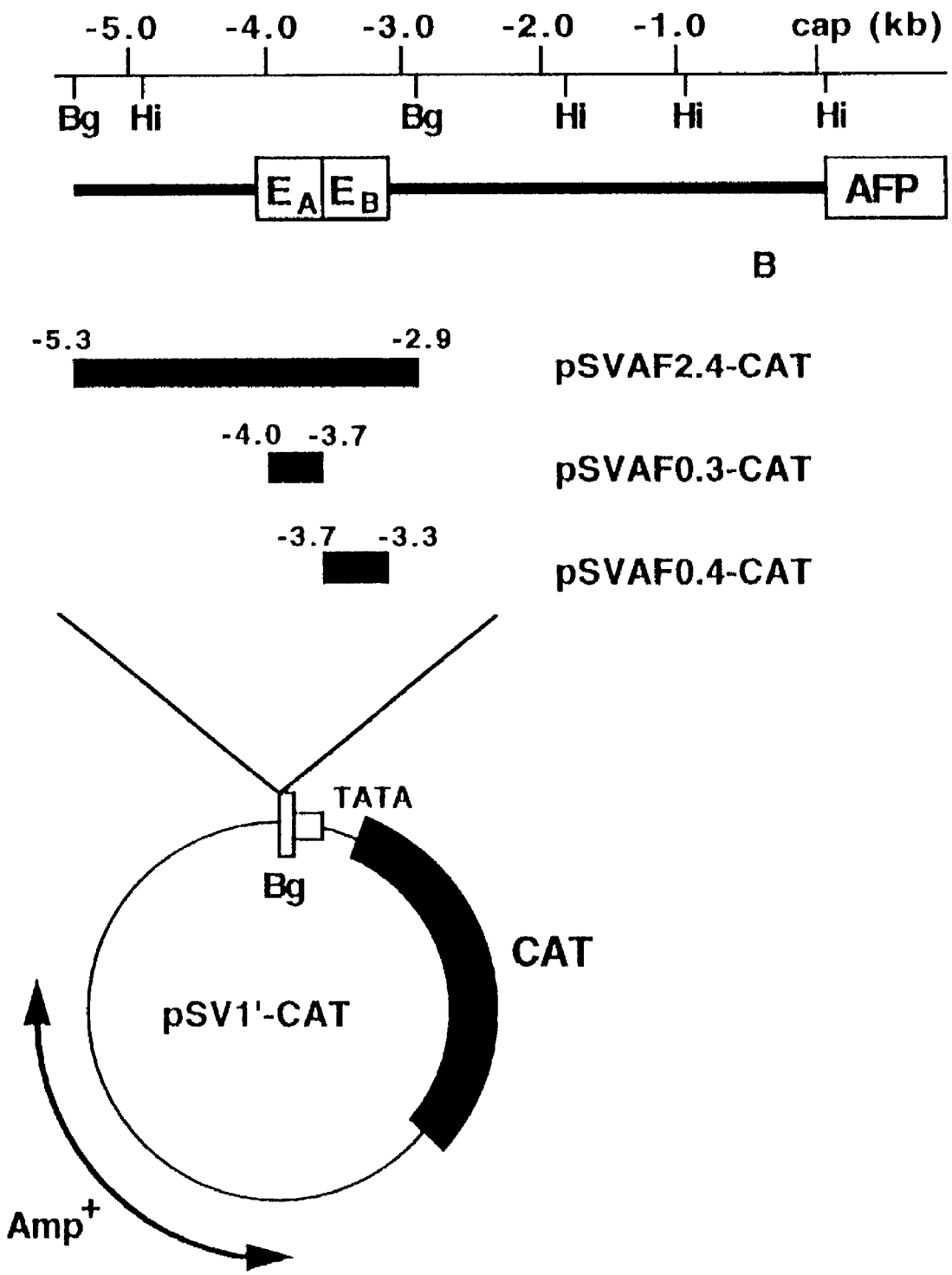
FIG_ID

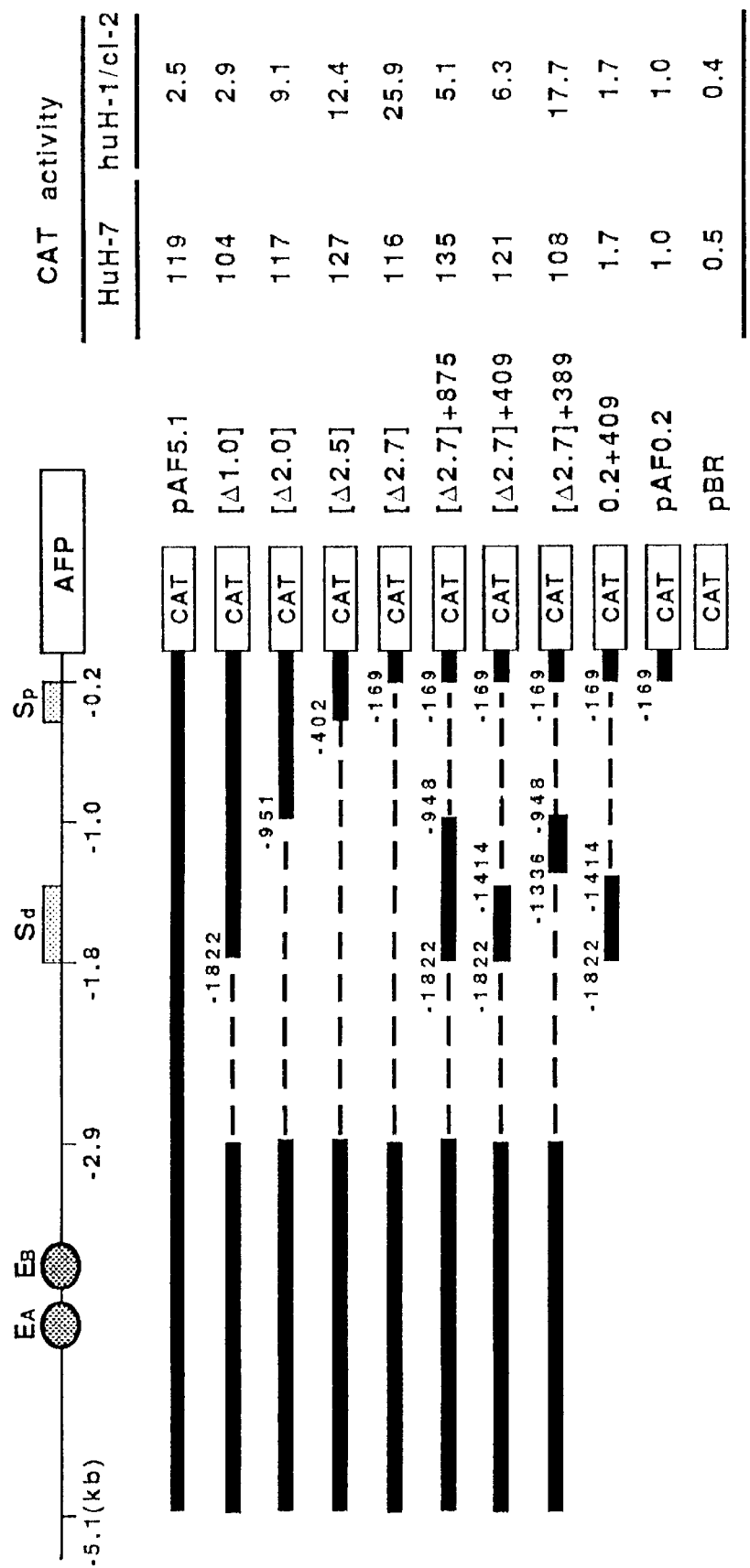
FIG_2

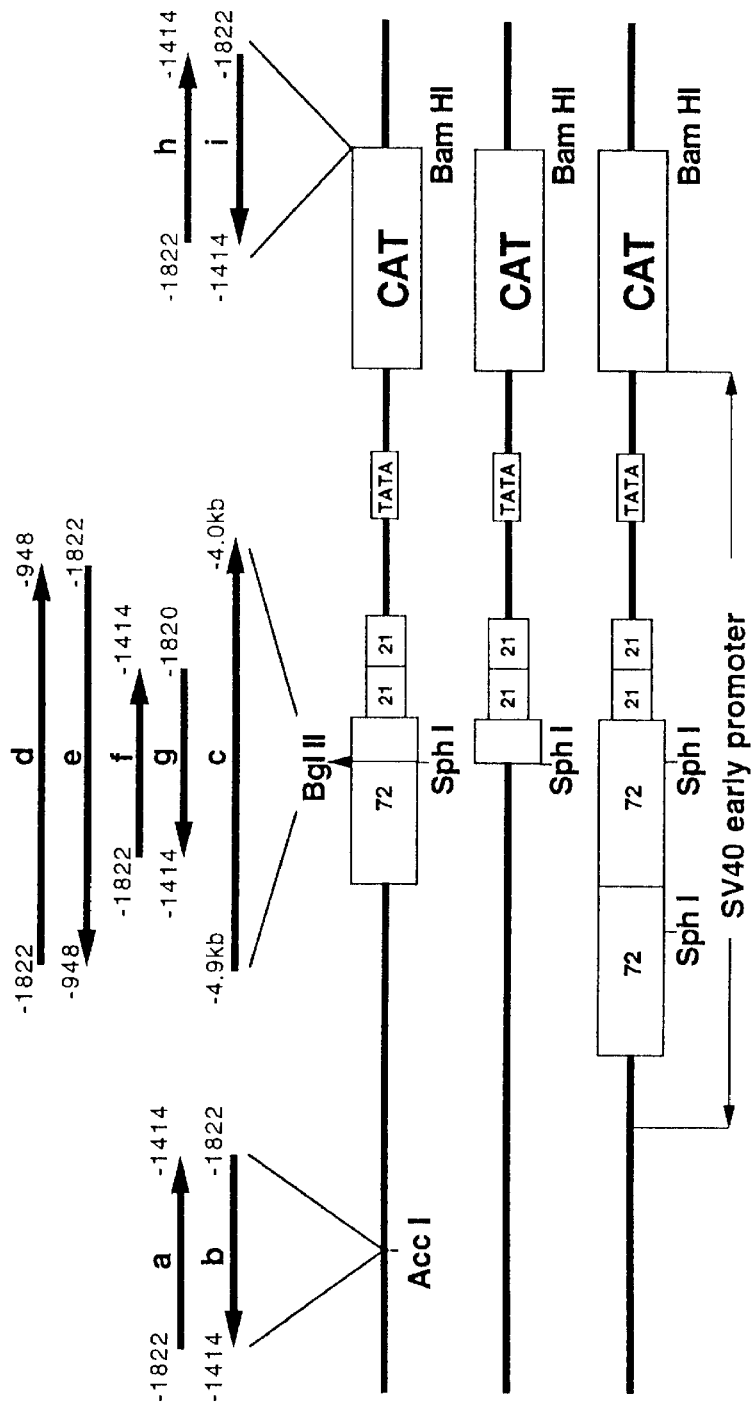
FIG._3A

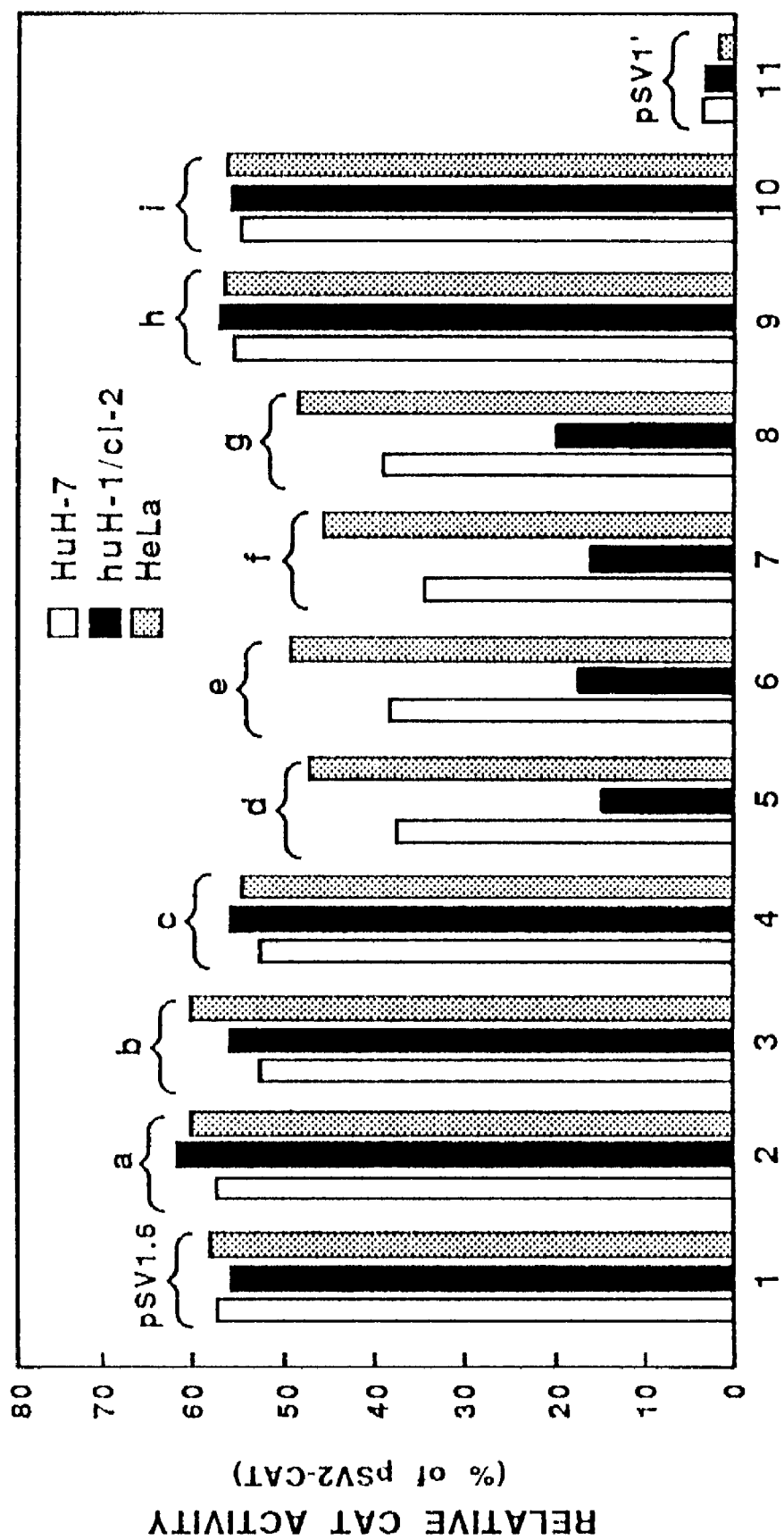
FIG_3B

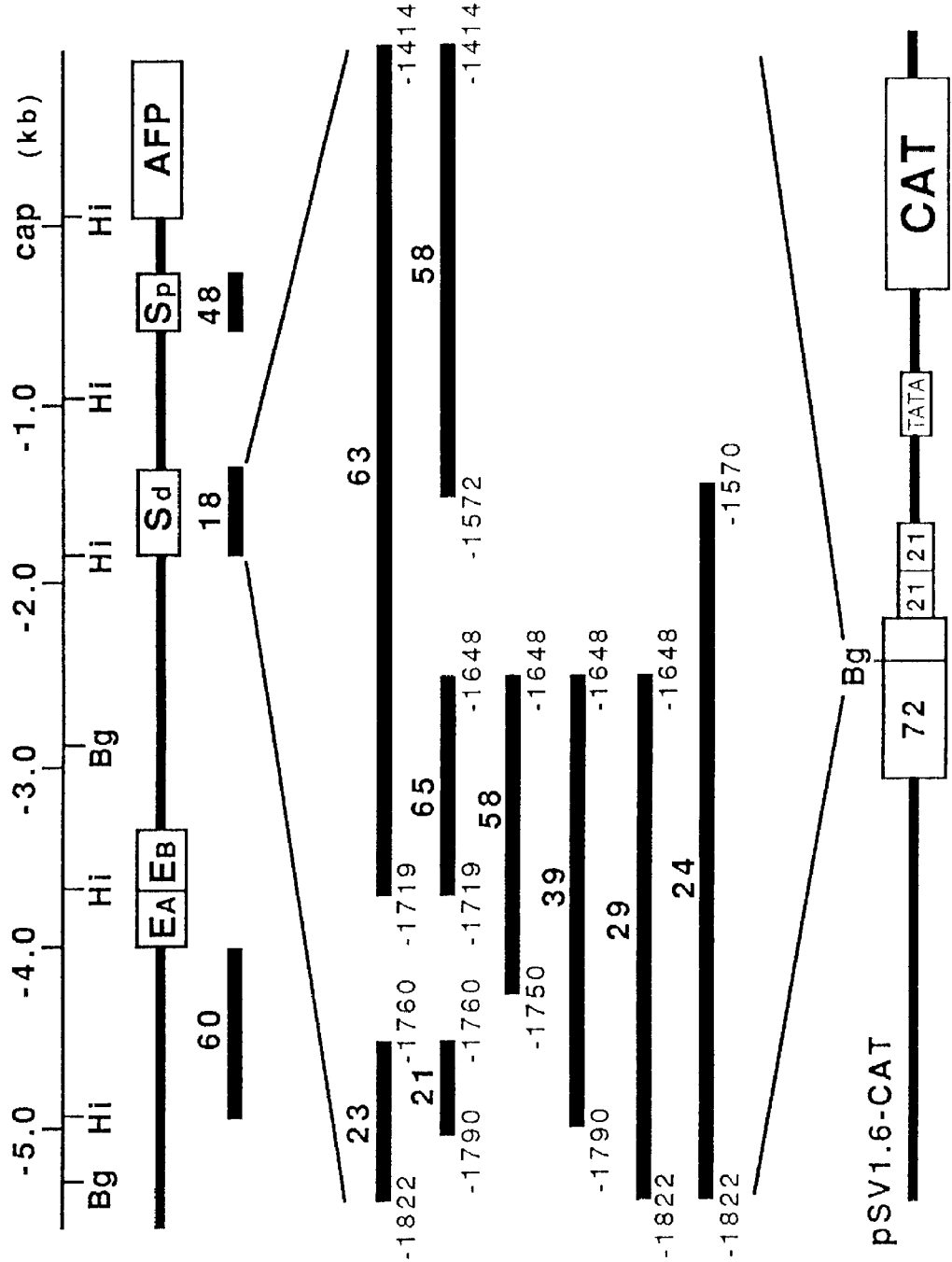
FIG_4

```
  [Δ1.0]
 ↑-1820          -1810       -1800       -1790       -1780       -1770       -1760       -1750
AG CTTATATAGT TTGCTTCATA AAACTCTATT TCAGTTCTTC ATAACTAATA CTTCATGACT ATTGCTTTTC AGTATTCCT
         -1740       -1730       -1720       -1710       -1700       -1690       -1680       -1670
TCATAACAAA TACTTTGGCT TTCATATATT TGAGTAAAGT CCCCCTTGAG GAAGAGTAGA AGAACTGCAC TTTGTAAATA

-1660       -1650       -1640       -1630       -1620       -1610       -1600       -1590
CTATCCTGGA ATCCAAACGG ATAGACAAGG ATGGTGCTAC CTCTTTCTGG AGAGTAGTG AGCAAGGCCT GTTTTGTTAA

-1580       -1570       -1560       -1550       -1540       -1530       -1520       -1510
CATGTTCCTT AGGAGACAAA ACTTAGGAGA GACACGCATA GCAGAAAATG GACAAAAACT AACAAATGAA TGGGAATTGT

-1500       -1490       -1480       -1470       -1460       -1450       -1440       -1430
ACTTGATTAG CATTGAAGAC CTTGTTTATA CTATGATAAA TGTTTGTATT TGCTGGAAGT GCTACTGACG GTAAACCCTT
-1414
TTTGTTT
```

FIG_5A

FIG. 5B

```
     [Δ2.5]
     ↓
       -400
-320    -310    -300    -290
TG GCATATGATA GCATTAAT AGTTTAAAG AATTAATGTA TTTAGATGAA TTGCATACCA AATCTGCTGT CTTTCTTTA

TGGCTTCATT AACTTAATTT GAGAGAAATT AATTATTCTG CAACTTAGGG ACAAGTCATC TCTTTGAATA TTCTGTAGTT
                                                                          [Δ2.7]
                                                                          ↓
                                -200
TGAGGAGAAT ATTTGTATA AAAATAAGTT TGCAAGTTTT TTTTTTCTGC CCCAAAGAGC TC
```

FIG. 5C

| | | | | | | | | | | | | Homology | |
|---|---|---|---|---|---|---|---|---|---|---|---|---|---|
| -1790 T C A G T T | C T T C A T | A A A | A A C T C T T A | T T -1790 | | | | | | | | | |
| -1807 | C T T C A T | A A | A T | A A C | T T | T T -1753 | C A T G A C T | | | | | 10/17 | nucleotides 16-32 of SEQ ID NO:6 |
| -1770 | C T T C A T | G A | T T | A C | C T | T T | | | | | | 14/17 | nucleotides 33-62 of SEQ ID NO:6 |
| -1761 T | | | | | | | | | | | | 16/17 | nucleotides 53-69 of SEQ ID NO:6 |
| -1742 | C T T C A T | A A | A A | A A | G C | T T -1725 | | | | | | 10/17 | nucleotides 81-97 of SEQ ID NO:6 |
| -317 | C T T C A T | T A | A A | A C T T A | A T | T T -300 | | | | | | 10/17 | nucleotides 86-102 of SEQ ID NO:7 |

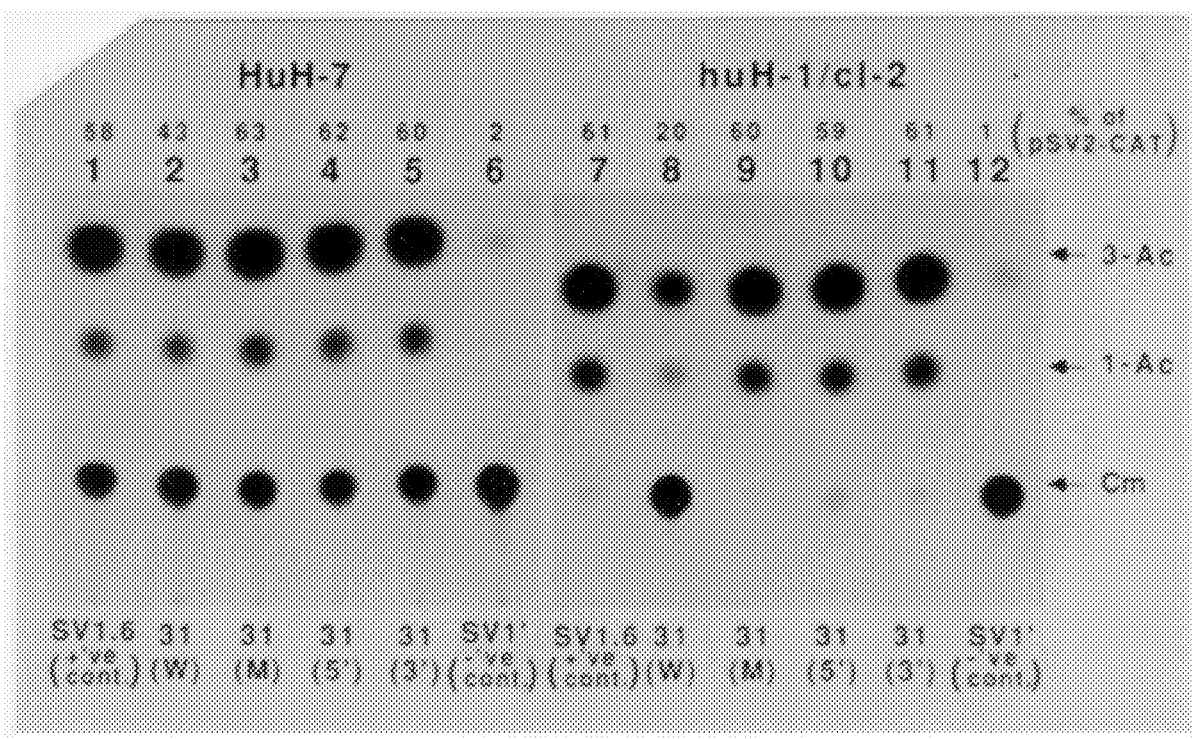
FIG_6A
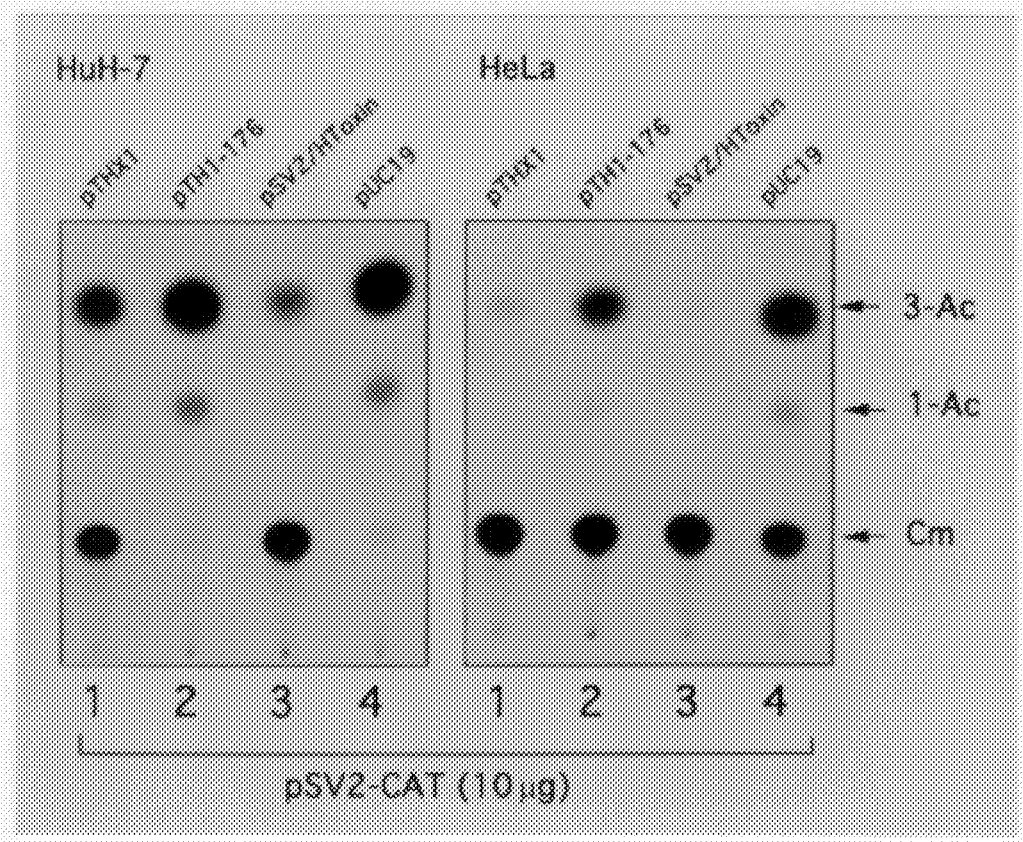
FIG_8

FIG_6B
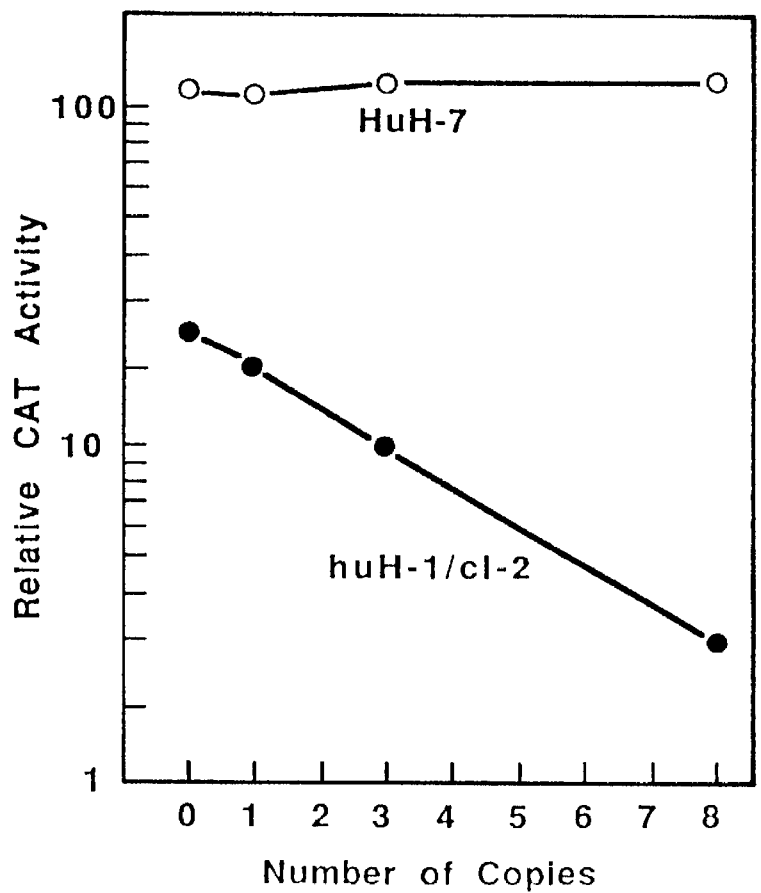
FIG_6C

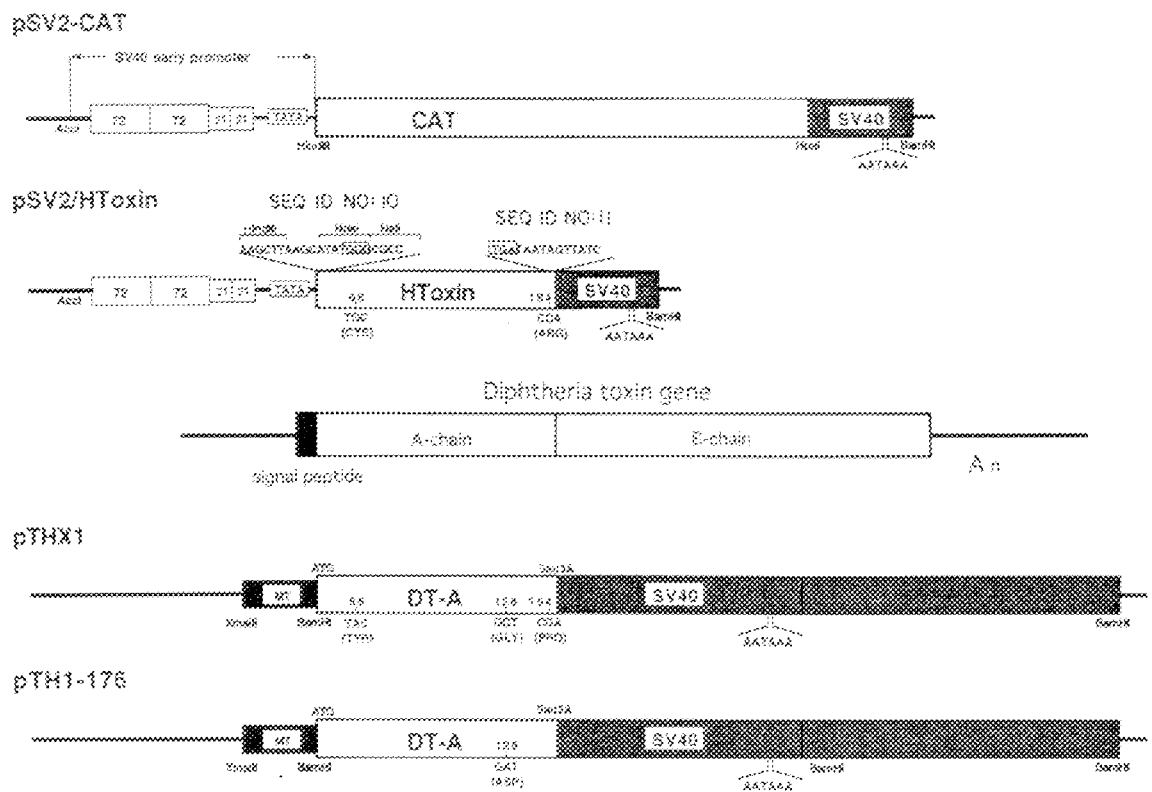
FIG_7

TRANSFORMATION FREQUENCY OF G418 RESISTANT COLONIES AFTER TRANSFECTION OF PLASMIDS

| Plasmids | No. of colonies/10⁵ cells | |
|---|---|---|
| | HuH-7 | HeLa |
| pMC1neo | 4.2 | 0.5 |
| pSV2/HToxin/neo | 0 | 0 |
| pUC19 | 0 | 0 |

Cells were replated in medium containing G418 after 2 days of transfection with 10 μg of plasmids. pMC1neo contained the neomycin resistant gene, pSV2/HT/neo contained HToxin and neomycin resistant gene as shown below, and pUC19 was used as negative control.

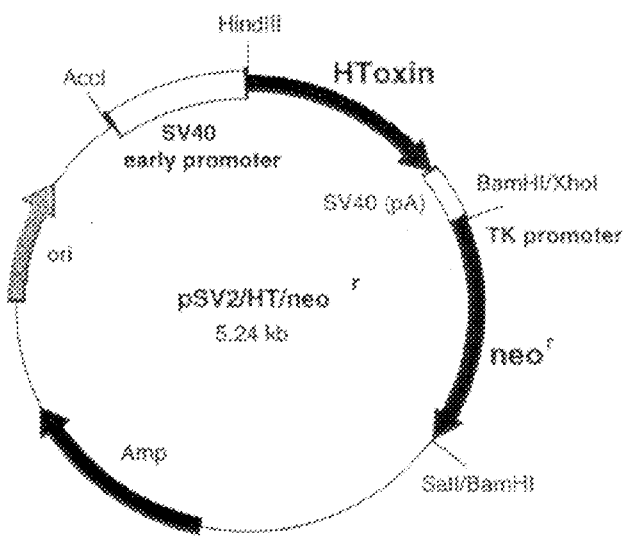

FIG_9

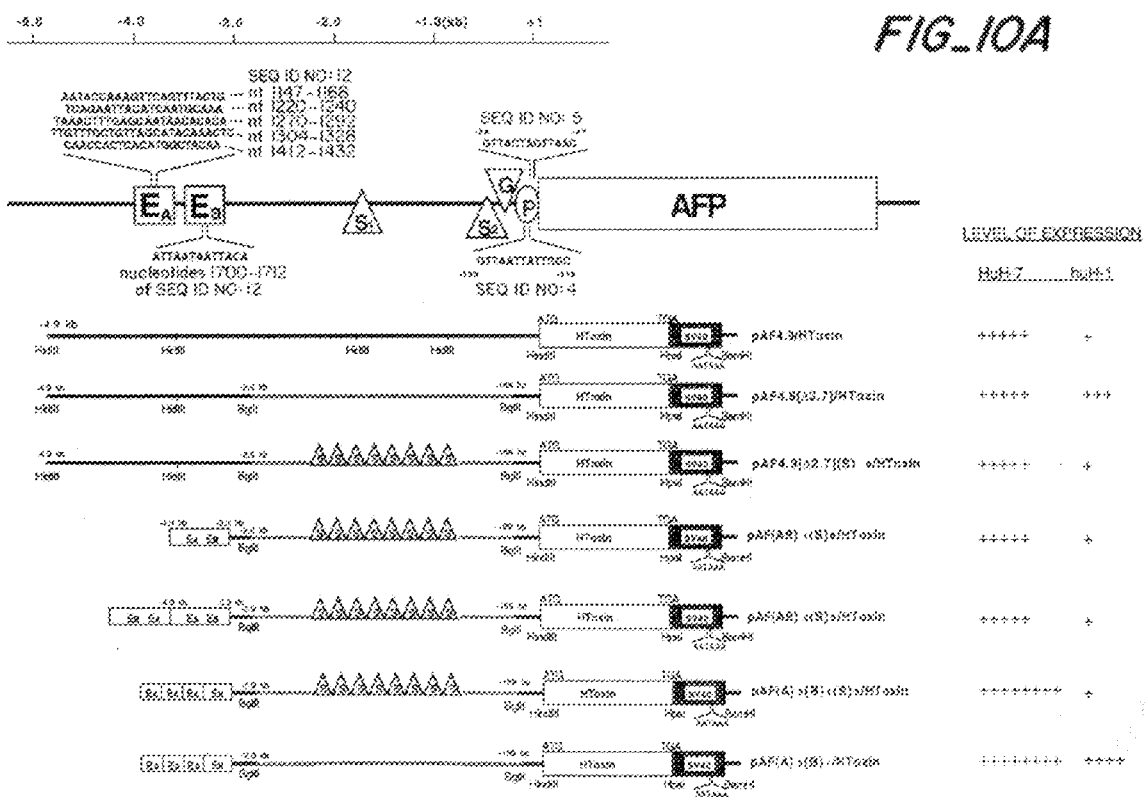
FIG_10A

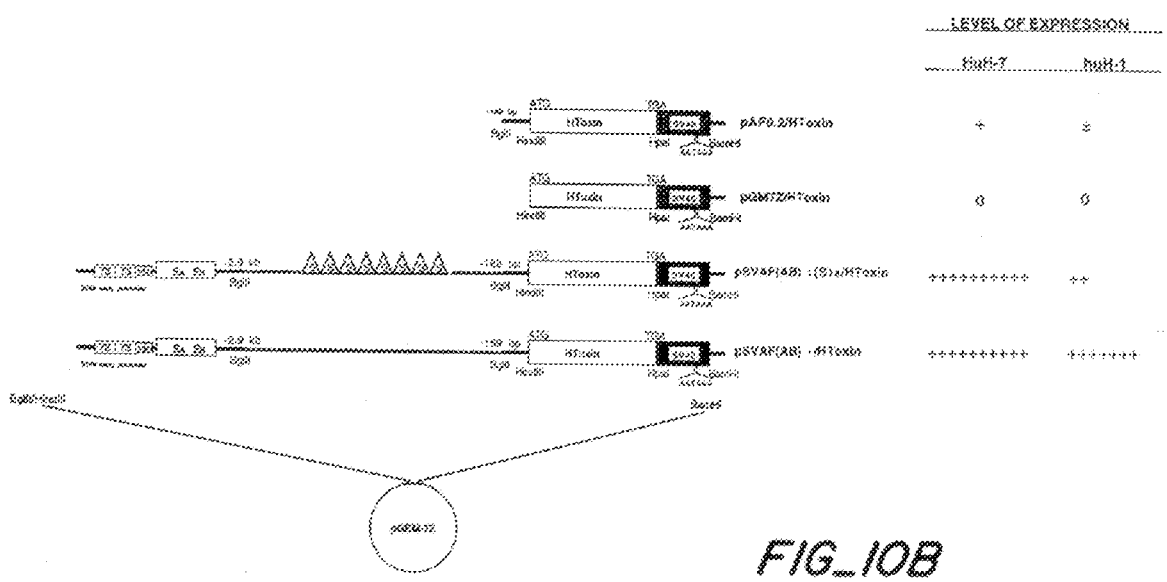
FIG_10B

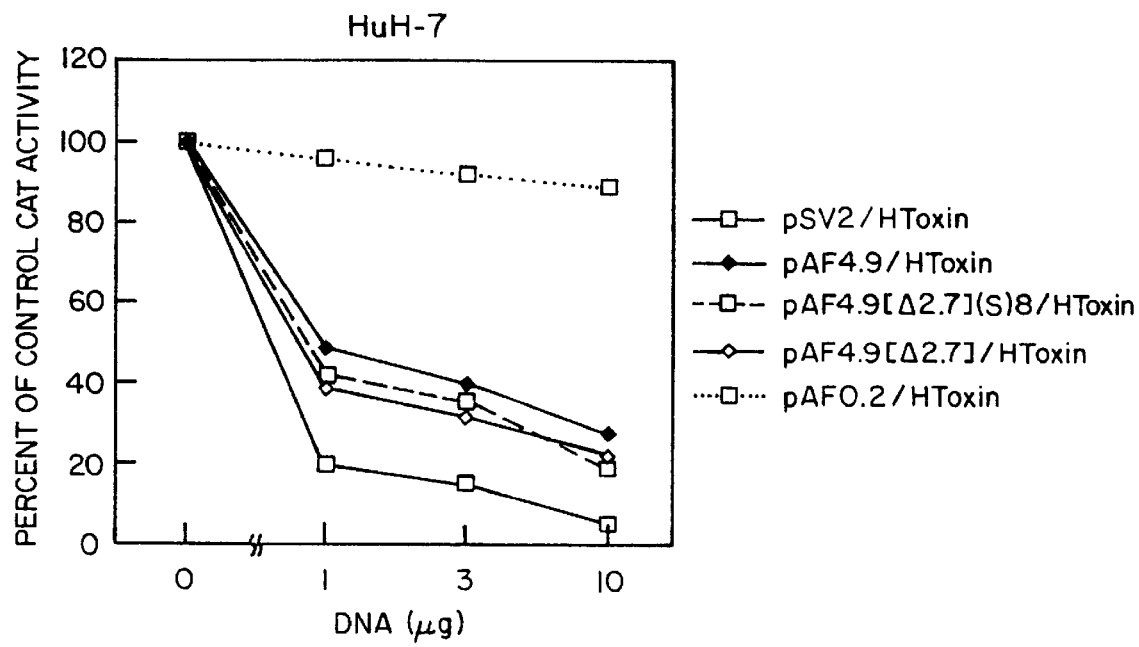
FIG_11A
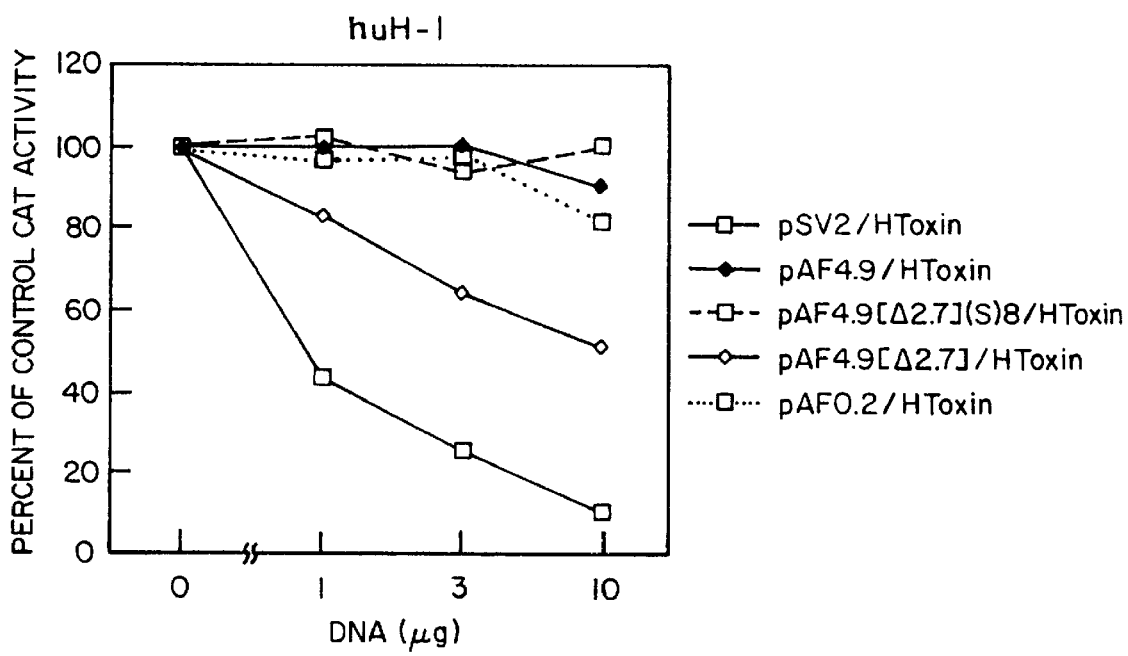
FIG_11B

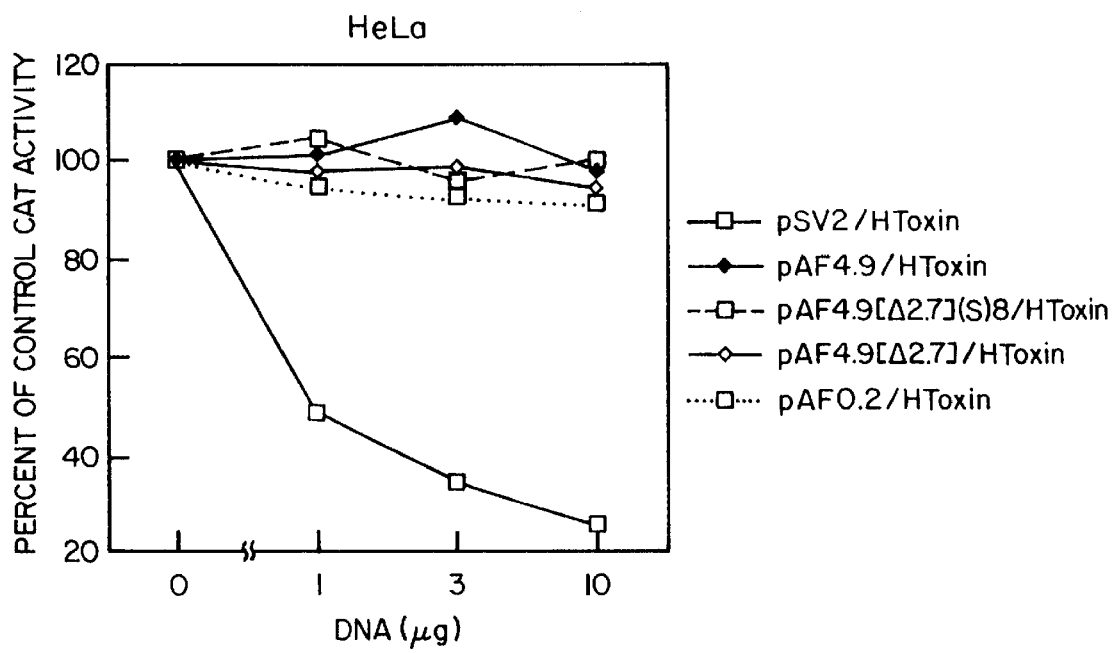
FIG_IIC
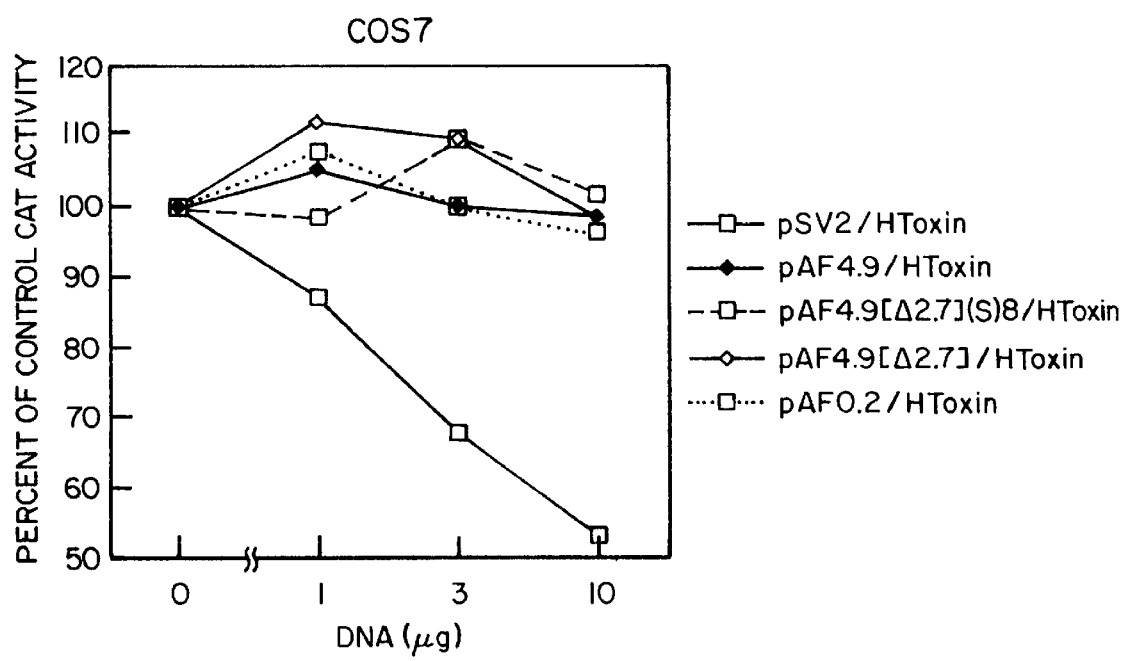
FIG_IID

```
-5.1K
     ┌─pAF 5.1-CAT
     GAATTCTTAGAAATATGGGGGTAGGGGTGTGGTGGTAATTCTGTTTTCACCCCATAGCTGAGATAAGCATTGGGTTAAATGTGCTTTCA  90
     EcoRI
▼▼▼▼▼▼▼▼▼▼▼▼
     CACACACATCACATTTCATAAGAATTAAGGAACAGACTATGGGCTGGAGGACTTTGAGGATGTCTGTCTCATAACACTTGGGTTGTATCT  180
                    ┌─pAF 4.9-CAT
     GTTCTATGGGGCTTGTTTTAAGCTTGCAACAGGGTTCACTGACTTTCTCCCCAAGCCCAAGGTACTGTCCTCTTTTCATATC  270
                    HindIII
     TGTTTTGGGGCCTCTGGGGCTTGAATATCTGAGAAAATATAAACATTTCAATAATGTTCTCTGGTGAGATGAGTATGAGAGATGTGTCAT  360
                  HaeIII
     TCATTTGTATCAATGAATGAGGACAATTAGTGTATAAATCCTTAGTACAACAATCTGAGGGTAGGGTGGTACTATTCAATTTCTA  450
     TTTTATAAAGATACTTATTCTATTTATTTATGCTTGTGACAAATGTTTGTTCGGACCACAGGAATCACAAAGATGAGTCTTTGAATTT  540
                                                         AvaII
     AAGAAGTTAATGGTCCAGGAATAATTACATAGCTTACAAATGACTATGATATACCATCAAACAAGAGGTTCCATGAGAAATAATCTGAA  630
     AGGTTTAATAAGTGTCAAGGTGAGAGGGCTCTTCTCTAGAGACTAATCAGAGAATACATTCAGGATAATTATTTGAATAGACCT  720
     TAAGGGTTGGTACATTTGTTCAAGCATTGATGGAGAAGGAGTGAATATTTGAAAACATTTCAACTAACCACCCAATCCAAC  810
     AAACAAAAAATGAAAAGAATCTCAGAACAGTGAGATAAGACAGTATAGCTCAACGTATAGCTCAACTGCTCTGAAGAA  900
▼▼▼▼▼▼▼
     GTATATATCTAATATTAACACTAACATCAGCTAATAATGATAATTACTGTCATTTTAAGTGTCTATAAGTACCAGGCATTTAGA  990
     AGATATTATTCCATTTATATATCAAAATAACTTGAGGGATAGATCATTTTCATGATATATGAGAAAAATTAAAAACAGATTGAATTAT  1080
```

*FIG_12A*

```
TTGCCTGTCATACAGCTAATAATTGACCATAAGACAATTAGATTTAAATTAGTTTTGAATCTTTCTAATACCAAAGTTCAGTTTACTGTT   1170

CCATGTTGCTTCTGAGTGGCTTCACAGACTTATGAAAAAGTAAACGGAATCAGAATTACATCAATGCAAAAGCATTGCTGTGAACTCTGT   1260

ACTTAGGACTAAACTTTGAGCAATAACACACATAGATTGAGGATTGTTTGCTGTTAGCATACAAACTCTGGTTCAAAGCTCCTCTTTATT   1350

GCTTGTCTTGGAAAATTTGCTGTTCTTTCATGGTTTCTCTTTCACTGCTATCTCTATTTTTCTCAACCACTCACATGGCTACAATAACTGTC   1440

TGCAAGCTTATGATTCCCAAATATCTCTAGCCTCAATCTGTTCCAGAAGATAAAAAGTAGTATTCAAATGCACATCAACGTCTCC   1530
    pAP 3.7-CAT
    HindIII ACTTGGAGGGCTTAAAGACGTTCAACATACAAAACCGGGGAGTTTGCCTGGAATGTTTCCTAAATGTGTCCTGTAGCACATAGGGTCC   1620
                                                                                    AvaII TCTTGTTCCTAAAATCTAATTACTTTAGCCCAGTGTCTCATCCCCACCTATGGGGAGATGAGAGTGAAAAGGGAGCCTGATTAATAATTA   1710

CACTAAGTCAATAGGCATAGAGCCAGGACTGTTTGGGTAAACTGGTCACTTTATCTTAAACTAAATATATCCAAAACTGAACATGTACTT   1800
                                                                                -3.3K

AGTTACTAAGTCTTTGACTTTATCTCATTCATCCAGGCCACTTATTTGACAGTATTATTGCGAAAACTTCCTAAC   1890
                                         HaeIII

TGGTCTCCTTATCATAGTCTTTATCCCCTTTTGAAACAAAAGAGACAGTTTCAAAATACAAATATGATTTTATTAGCTCCCTTTGTTGT   1980

CTATAATAGTCCCAGAAGGAGTTATAAACTTCCATTTAAGAGATCTTTGAGATGTGGCCCTTGCCAACTTTGCCAGGAATTCCAATATCT   2070
                                                                            EcoRI

AGTATTTTCTACTATTAAACTTTGTGCCTCTTCATTTTCTCAAAACTGCATTCCCTAAGTGTGCATTGTTTCCCTTACCGGTTGGTT   2160

TTTCCACCACCTTTTACATTTCCTGGAACACTATACCCCCTCCTTCATTGGCCACCTCTAATTTTCTTTCAGATCT   2240
                                                                    pAP 2.9-CAT
                                                HaeIII               BglII

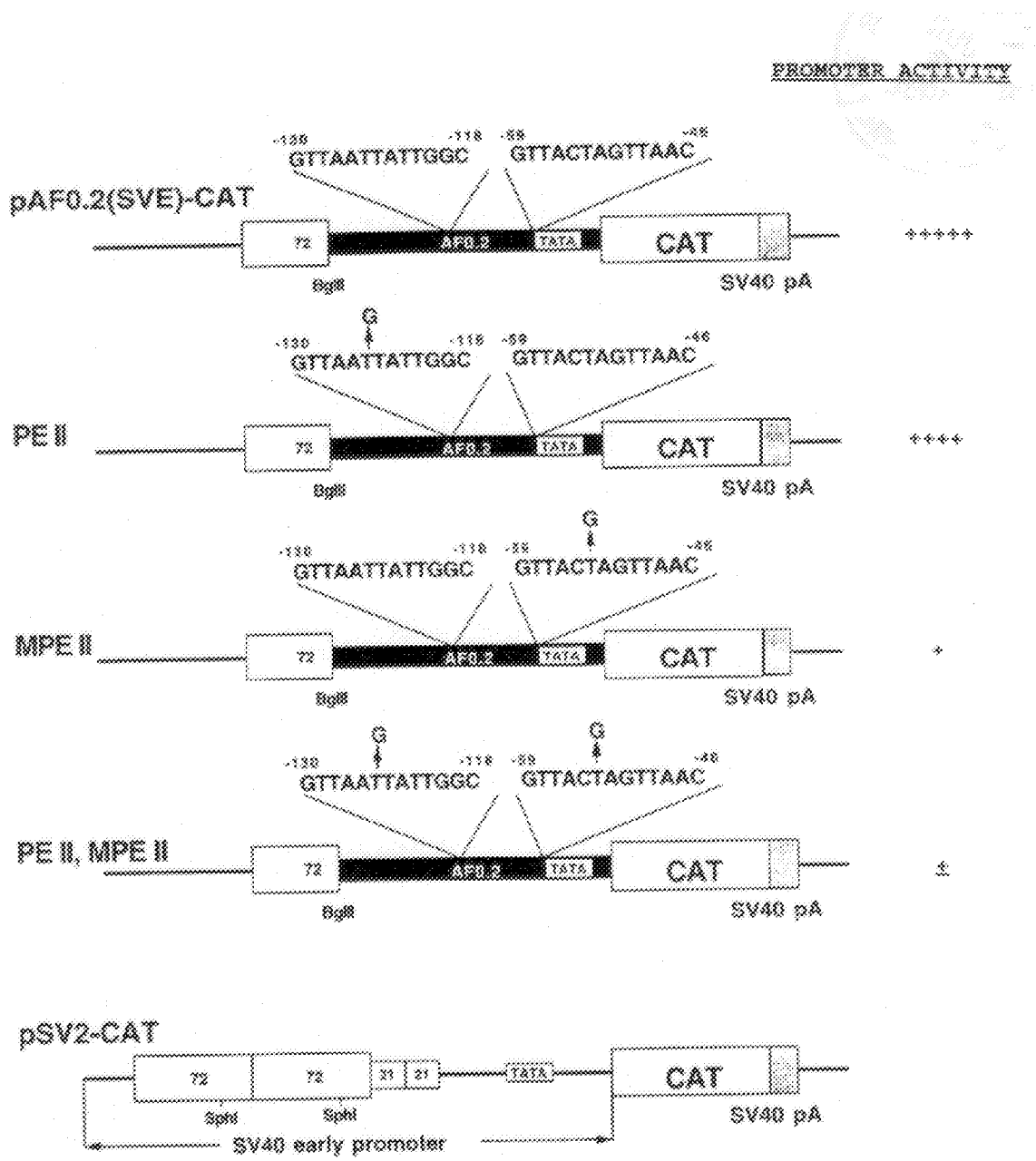
FIG_13

| SEQ ID NO: | Synthetic Olignonucleotide Sequences | Relative CAT activity | |
|---|---|---|---|
| | | 1 copy | 3 copies |
| 15 | Enhancer Domain A1 Wild-type<br>5'-AATTCTTTCTAATACCAAAGTTCAGTTTACTGTTCCA-3'<br>3'-GAAAGATTATGGTTTCAAGTCAAATGACAAGGTCTAG-5' | 6.8 | 52.4 |
| 16 | Enhancer Domain A1 Mutant<br>• • • •<br>5'-AATTCTTTCTAATACCGACGCTCCGTTTACTGTTCCA-3'<br>3'-GAAAGATTATGGCTGCGAGGCAAATGACAAGGTCTAG-5' | 1.4 | - |
| 17 | Enhancer Domain A2 Wild-type<br>5'-GATCAGAATTACATCAATGCAAA-3'<br>3'-TCTTAATGTAGTTACGTTTCTAG-5' | 3.8 | 42.2 |
| 18 | Enhancer Domain A2 Mutant<br>• • •<br>5'-GATCACAATTACGTCAACGCAAA-3'<br>3'-TGTTAATGCAGTTGCGTTTCTAG-5' | 1.8 | - |
| 19 | Enhancer Domain A3 Wild-type<br>5'-GATCTTGTTTGCTGTTAGCATACAAACTC-3'<br>3'-AACAAACGACAATCGTATGTTTGAGCTAG-5' | 3.2 | 32.5 |
| 20 | Enhancer Domain A3 Mutant<br>• • • •<br>5'-GATCTAGCTTGCTGTTAGCATACCAGACTC-3'<br>3'-ATCGAACGACAATCGTATGGTCGAGCTAG-5' | 0.9 | 18.3 |
| 21 | Enhancer Domain A4 Wild-type<br>5'-GATCTATTTTTCTCAACCACTCACATGGCTACAA-3'<br>3'-ATAAAAAGAGTTGGTGAGTGTACCGATGTTCTAG-5' | 2.4 | 28.0 |
| 22 | Enhancer Domain A4 Mutant<br>• •<br>5'-GATCTATTTTTCTCAACTACCCACATGGCTACAA-3'<br>3'-ATAAAAAGAGTTGATGGGTGTACCGATGTTCTAG-5' | - | 1.2 |
| 23 | Enhancer Domain B Wild-type<br>5'-GATCCTGATTAATAATTACACTAAGTCAA-3'<br>3'-GGACTAATTATTAATGTGATTCAGTTCTAG-5' | 3.3 | 34.5 |
| 24 | Enhancer Domain B Mutant<br>•<br>5'-GATCCTGATTAATAAGTACACTAAGTCAA-3'<br>3'-GGACTAATTATTCATGTGATTCAGTTCTAG-5' | 1.3 | - |
| 8 | Silencer Sd Wild-type<br>5'-GATCTCAGTTCTTCATAACTAATACTTCATGACTA-3'<br>3'-AGTCAAGAAGTATTGATTATGAAGTACTGATCTAG-5' | 60 | 12.8 |
| 25 | Silencer Sd Mutant<br>• • • •<br>5'-GATCTCAGTTGTTCGTAACTAAGACTTCATGACTA-3'<br>3'AGTCAACAAGCATTGATTCTGAAGTACTGATCTAG-5' | 125 | - |

FIG_14

Diphtheria Toxin A chain

```
  +1  GCAGGCGCTG ATGATGTTGT TGATTCTTCT AAATCTTTTG TGATGGAAAA CTTTTCTTCG TACCACGGGA CTAAACCTGG
 +81  TTATGTAGAT TCCATTCAAA AAGTATACA  AAGCCAAAA  TCTGGTACAC AAGGAAATTA TGACGATGAT TGGAAAGGGT
+161  TTTATAGTAC CGACAATAAA TACGACGCTG CGGATACTC  TGTAGATAAT GAAACCCGC  TCTCTGGAAA AGCTGGAGGC
+241  GTGGTCAAAG TGACGTATCC AGGACTGACG AAGTTCTCG  AGGAAGAGT  GGATAATGCC GAAACTATTA AGAAAGAGTT
+321  AGGTTAAGT  CTCACTGAAC CGTTGATGGA GCAAGTCGGA ACGGAAGAGT TTATCAAAAG GTTCGGTGAT GGTGCTTCGC
+401  GTGTAGTGCT CAGCCTTCCC TTCGCTGAGG GGACTTCTAG CGTTGAATAT ATTAATAACT GGGAACAGGC GAAAGCGTTA
+481  AGCGTAGAAC TTGAGATTAA TTTTGAAACC CGTGGAAAAC GTGGCCAAGA TGCGATGTAT GAGTATATGG CTCAAGCCTG
+561  TGCAGGAAAT CGTGTCAGGC GA
```

```
  1  ala-gly-ala-asp-asp-val-val-asp-ser-ser-lys-ser-phe-val-met-glu-asn-phe-ser-ser-
 21  tyr-his-gly-thr-lys-pro-gly-tyr-val-asp-ser-ile-gln-lys-gly-ile-gln-lys-pro-lys-
 41  ser-gly-thr-gln-gly-asn-tyr-asp-asp-trp-lys-gly-phe-tyr-ser-thr-asp-asn-lys-
 61  tyr-asp-ala-ala-gly-tyr-ser-val-asp-asn-glu-asn-pro-leu-ser-gly-lys-ala-gly-gly-
 81  val-val-lys-val-thr-tyr-pro-gly-leu-thr-lys-val-leu-ala-leu-lys-val-asp-asn-ala-
101  glu-thr-ile-lys-lys-glu-leu-gly-leu-ser-leu-thr-glu-pro-leu-met-glu-gln-val-gly-
121  thr-glu-glu-phe-ile-lys-arg-phe-gly-asp-gly-ala-ser-arg-val-val-leu-ser-leu-pro-
141  phe-ala-glu-gly-ser-ser-val-glu-tyr-ile-asn-asn-trp-glu-gln-ala-lys-ala-leu-
161  ser-val-glu-leu-glu-ile-asn-phe-glu-thr-arg-gly-lys-arg-gly-gln-asp-ala-met-tyr-
181  glu-tyr-met-ala-gln-ala-cys-ala-gly-asn-arg-val-arg-arg-
```

FIG_15A

HToxin

```
  +1  ATGGGCGCCG ATGATGTTGT TGATTCTTCT AAATCTTTTG TGATGGAAAA CTTTTCTTCG TACCACGGGA CTAAACCTGG
 +81  TTATGTAGAT TCCATTCAAA AAGGTATACA AAGCCAAAA  TCTGGTACAC AAGGAAATTA TGACGATGAT TGGAAGGGT
+161  TTTATAGTAC CGACAATAAA TACGACGCTG CGGGATGCTC TGTAGATAAT GAAAACCCGC TCTCTGGAAA AGCTGGAGGC
+241  GTGGTCAAAG TGACGTATCC AGGGCTGACG AAGGTTCTCG CACTAAAAGT GGATAATGCC GAAACTAT

METHOD OF EXPRESSING GENES IN MAMMALIAN CELLS

BACKGROUND OF THE INVENTION

1. Field of the Invention

The present invention relates to a method of expressing a heterologous gene in mammalian cells, and a recombinant DNA construct for use in the method. More particularly the invention relates to a recombinant DNA obtained by linking a gene coding for a cancer-cell toxin to certain of the transcriptional regulatory regions of the human α-fetoprotein (AFP) gene so that the toxin gene is transcribed selectively in hepatic cancer cells.

2. Description of the Related Art

Cancer of all forms is one of the major causes of morbidity throughout the world. Research in the area of cancer chemotherapy has produced a variety of antitumor agents which have differing degrees of efficacy. A variety of cancer-therapeutic agents are known, for example, alkylating agents, antimetabolites, alkaloids and carcinostatic antibiotics. Standard clinically used agents include adriamycin, actinomycin D, methotrexate, 5-fluorouracil, cis platinum, vincristine and vinblastine. However, these presently available antitumor agents are known to have various disadvantages such as toxicity to healthy cells and resistance of certain tumor types.

Hepatocellular carcinoma (HCC) is one of the major malignant diseases in the world today; the greatest incidence being in Japan, China, other parts of the Asia and sub-Saharan Africa. Recent evidence suggests that the incidence of hepatocellular carcinoma in Europe and North America is increasing. The disease is estimated to be responsible for or involved in up to approximately 1,250,000 deaths a year and as such is numerically one of the world's major malignant diseases.

The prognosis of HCC is poor with the world-wide frequency rate almost equalling the mortality rate. After diagnosis, the median survival time is less than four months. Long-term survival, defined as survival longer than one year after the diagnosis, is seen only occasionally. Most HCC patients succumb to either the complications of liver failure with or without massive bleeding, or to the general effects of a large tumor burden, with cachexia, malnutrition, infection and sepsis. Though distant metastases occur (up to 90% of patients have metastatic tumors at the time of death), hepatic disease most often limits survival. Consequently, therapies directed towards the control of hepatic tumors are appropriate, although it will be appreciated that treatment of the metastatic disease is also of great importance. (Berk. P. (Ed) Seminars in Liver Disease 4, No. 2, Thieme-Stratton Inc. New York, N.Y. (1984).

Current therapies available to the clinician are on the whole ineffective as a cure for this disease (Nerenstone et al., Cancer Treatment Review 15, 1–31 (1988). Systemic single and combination agent chemotherapy and radiation are relatively ineffective. Since a cancer cell of a patient originates from a normal cell of the same patient, these known agents fail to clearly discriminate cancer cells from normal cells, thus causing various adverse effects. Therefore, use of the known cancer-therapeutic agents is significantly limited in various ways.

To date, surgery continues to be the only potential cure. However, at the time of diagnosis, the overwhelming majority of patients are not able to undergo radical surgery. In certain studies (Nerenstone et al. supra) it was found that less than 3% of patients were considered capable of undergoing surgery and of the small percentage that do, approximately 50% suffer from postoperative morbidity (Nerenstone et al. supra). However, it is appreciated by those skilled in the art that novel approaches and entities for cancer therapies are required.

Gene therapy involves the stable integration of new genes into particular target cells and the expression of those genes, once they are in place, to alter the phenotype of that particular target cell (for review see Anderson, W. F. Science 226: 401–409, 1984; McCormick, D. Biotechnology 3: 690–693, 1985).

Genetic ablation takes advantage of tissue specificity of certain gene regulatory elements to express a toxin gene in a cell specific manner. For example, Goring et al. (1987) Science 235: 456–458 have shown that the γ2-crystallin promoter is able to direct expression of a linked lacZ gene in the lens fiber cells in transgenic mice in a developmental manner. When the diphtheria toxin A-chain (DT-A) gene is expressed in a similar manner in the lens fiber cells in mice, microphthalmic mice having lenses deficient of fiber cells are obtained (Brietman et al., (1987) Science 238: 1563–1565). When an attenuated DT-A gene (tox 176) is used, transgenic mice which displayed predominately cataracts or clinical anophthalmia were obtained (Brietman et al. (1990) Mol. Cell Biol. 10: 474–479).

Palmiter et al. (1987) Cell 50: 435–443 have used the elastase I promoter/enhancer to drive the expression of the DT-A gene in pancreatic acinar cells to yield mice lacking a normal pancreas.

Alternatively, the expression of a gene encoding an enzyme capable of selective conversion of chemical agents to cytotoxic or cytostatic metabolites has been proposed. (European Patent Application No. 0 415 731). A molecular chimaera is constructed which consists of a natural transcriptional regulatory region attached to a gene encoding an enzyme which is capable of converting a metabolite into the toxin. Upon administration of the molecular chimaera to the patient and the metabolite, the enzyme is expressed in the cancer cells, which enzyme converts the metabolite into the toxin thereby killing the cancer cells. However, this procedure requires the administration of two chemicals. Also, the possibility exists that the metabolite may be converted into the toxin in the incorrect cells resulting in toxicity to normal cells. A method of controlling the expression of a toxin gene in cancer cells would be useful.

SUMMARY OF THE INVENTION

The present invention is directed to a method of expressing a heterologous gene in mammalian cells and to a recombinant DNA construct for use in the method.

Accordingly, one aspect of the present invention provides a method of expressing a heterologous gene in a mammalian cell comprising inserting a DNA construct into a mammalian cell, said construct comprising an AFP enhancer region and an AFP promotor region functionally linked to the heterologous gene in the absence of an AFP silencer region, and expressing the heterologous gene in the mammalian cells.

Another aspect of the present invention provides a method of killing cells which constitutively express AFP comprising inserting a DNA construct into a mammalian cell, said construct comprising an enhancer region, an AFP silencer region and a promoter sequence functionally linked to a direct toxin gene and expressing the toxin gene in the mammalian cells under conditions such that only cells which constitutively express AFP are killed.

Also provided are mutated enhancer domains and silencer regions useful in the methods of this invention.

Further advantages of the present invention will become apparent from the following description of the invention with reference to the attached drawings.

BRIEF DESCRIPTION OF THE DRAWINGS

FIG. 1A illustrates CAT fusion genes containing the human albumin and α-fetoprotein (AFP) 5'-flanking regions. Positions of the enhancers ($E_1$ (SEQ ID NO:1), $E_A$ and $E_b$ (nucleotides 1700 to 1712 of SEQ ID NO:12)), promoters (P) (SEQ ID NOS:2,3,4 and 5), glucocorticoid—responsive element (G) and AT-rich elements are also indicated.

FIG. 1B illustrates CAT activities expressed in HuH-7 and huH-1/cl-2 cells transfected with the CAT fusion genes shown in FIG. 1A. CAT activities as a percentage of pSV2-CAT activity are shown above the autoradiograms. Cm—chloramphenicol; 1-Ac, 1-acetate chloramphenicol; 3-Ac, 3-acetate chloramphenicol.

FIG. 1C illustrates the effects of dexamethasone on CAT activities in HuH-7 and huH-1/cl-2 cells transfected with pAF1.0-CAT. Cm, 1-Ac and 3-Ac are as defined in FIG. 1B. + and − indicate the presence and absence of dexamethasone respectively.

FIG. 1D illustrates the AFP enhancer/SV40 early promoter fusion genes; Hi, Hind III; Bg, BglII.

FIG. 2 illustrates the detection of silencer activities by deletion analysis. The precise end points of the deletion are indicated in base pairs from the AFP cap site. The closed bars indicate AFP 5'-flanking sequences and the dotted lines indicate deleted sequences. The CAT activities are expressed relative to pAFO.2(Bg)-CAT(pAFO.2) which contains the 169 bp AFP promoter region.

FIG. 3A illustrates the plasmids constructed to test the effect of the position of the silencer region.

FIG. 3B illustrates the position dependent suppression of SV40 enhancer activity by the Sd silencer region. This figure shows the CAT activities expressed in HuH-7, huH-1/cl-2 and HeLa cells after transfection with CAT fusion genes shown in FIG. 3A. The smaller letters correspond to the plasmid constructs in FIG. 3A.

FIG. 4 illustrates the silencer region. The endpoints of deletion are indicated in base pairs from the AFP cap site. CAT activities expressed are shown as percentages of the pSV2-CAT activity above the corresponding fragments. Hi, Hind III; Bg, BglII.

FIG. 5A illustrates the nucleotide sequence of the human AFP distal silencer regions (SEQ ID NO:6). The 17 bp repeated elements are underlined.

FIG. 5B illustrates the nucleotide sequence of the human AFP proximal silencer region (SEQ ID NO:7). The 17 bp repeated element is underlined.

FIG. 5C is a comparison of the 17 bp repeated elements in the distal and proximal silencer regions.

FIG. 6A illustrates the CAT activity of constructs having the 31 bp silencer region. $C_m$, 1-Ac and 3-Ac are as defined in FIG. 1B.

FIG. 6B illustrates the nucleotide sequences of the wild-type (SEQ ID NO:8) and mutant (SEQ ID NO:9) fragments.

FIG. 6C illustrates the relationship between the number of copies of the 31 bp Sd fragment and transcription suppressive activity.

FIG. 7 illustrates the structure of the diphtheria toxin gene and restriction maps of pSV2-CAT, pSV2/HToxin (SEQ ID NOS:10 and 11), pTHXl and pTHl-176.

FIG. 8 indicates the CAT activities expressed in HuH-7 and HeLa cells transfected with pSV2-CAT together with pSV2/H Toxin, pTHl-176 or pUC19.

FIG. 9 illustrates a restriction map of a pSV2/HT/neo$^r$ plasmid into which a neomycin-resistant gene was incorporated and shows the transformation frequency of G418 resistant colonies after transfection with various plasmids.

FIG. 10A illustrates restriction maps of: a DNA fragment containing the AFP gene and the transcriptional regulatory elements (a promoter P (SEQ ID NO:4 and 5), enhancers $E^A$ (nucleotide regions from SEQ ID NO:12) and $E^B$ (nucleotides 1700 to 1712 of SEQ ID NO:12), silencers $S_1$ (SEQ ID NO:6) and $S_2$ (SEQ ID NO:7) and a glucocorticoid reactive site G) located in the 5'-flanking region of the AFP gene; pAF4.9/HToxin; pAF4.9[Δ2.7]/HToxin; pAF4.9 [Δ2.7] (S) $_8$/HToxin; pAF(AB)$_2$(S)$_8$/HToxin; pAF(AB)$_1$(S) $_8$/HToxin; pAF(A)$_2$(B)$_1$(S)$_8$/HToxin; pAF(A)$_3$(B)$_1$/HToxin; pAF0.2/HToxin; and pGEM/HToxin. The relative levels of CAT expression from pSV2-CAT in HuH-7 and huH-1/cl-2 cells transfected with the above plasmids are indicated.

FIG. 10B illustrates the restriction maps of pSVAF(AB)$_1$(S)$_8$/HToxin and pSVAF(AB)$_1$/HToxin. The relative levels of expression from pSV2-CAT in HuH-7 and huH-1/cl-2 cells transfected with the above plasmids are indicated.

FIG. 11A is a graph indicating the dose-dependency of the killing effect of various recombinant plasmids on HuH-7 cells.

FIG. 11B is a graph indicating the dose-dependency of the killing effect of various recombinant plasmids on huH-1/cl-2 cells.

FIG. 11C is a graph indicating the dose-dependency of the killing effect of various recombinant plasmids on HeLa cells.

FIG. 11D is a graph indicating the dose-dependency of the killing effect of various recombinant plasmids on COS7 cells.

FIG. 12 is the nucleotide sequence of 2.2 kb DNA between −5.1 and −2.9 kb of the human AFP gene (SEQ ID NO:12). The 408 bp region used to construct pSVAF0.4-CAT is boxed. The solid arrow indicates an enhancer core sequence.

FIG. 13 illustrates the various mutant AFP promoters (PEII (SEQ ID NO:13) and MPEII (SEQ ID NO:14)). "72" indicates the 72 bp repeats from the $SV_{40}$ regulatory region.

FIG. 14 illustrates the relative CAT activity observed with various wild-type and mutant AFP enhancers and wild-type and mutant silencers.

FIG. 15A illustrates the DNA (SEQ ID NO:26) and amino acid sequence (SEQ ID NO:27) of the Diphtheria Toxin A-chain.

FIG. 15B illustrates the DNA (SEQ ID NO:28) and amino acid sequence (SEQ ID NO:29) of the HToxin gene.

DESCRIPTION OF THE PREFERRED EMBODIMENTS

The present invention relates to a method for controlling the expression of a heterologous gene in mammalian cells. The invention also relates to a method of destroying cancerous cells and a recombinant DNA construct for use in such a method. Specifically, the present invention provides for the combination of certain elements from the 5' regulatory region of the α-fetoprotein gene functionally linked to a heterologous gene for expression in mammalian cells. In particular, it has been found that by combining different silencer, enhancer and promoter elements, it is possible to control the level of expression of a heterologous gene functionally linked to the transcriptional regulatory region.

The albumin (ALB) and α-fetoprotein (AFP) genes exhibit extensive homology with regard to nucleic acid sequence, gene structure, amino acid sequence and protein secondary folding (for review see Ingram et al. PNAS 78 4694–4698 (1981). These genes are independently but reciprocally expressed in ontogeny. In normal development ALB transcription steadily increases with fetal growth and continues at a high level throughout adulthood. Transcriptional expression of ALB in the adult is confined to the liver. AFP is normally expressed in the yolk sac in fetal liver, and the fetal gastrointestinal tract, but declines after birth and is hardly detectable in non-pathologic or non-regenerating adult liver or in other normal adult tissue. However, AFP transcription in adult liver often increases dramatically in hepatocellular carcinoma (HCC). In addition, transcription may also be elevated in non-seminomatous and fixed carcinoma of the testis; in endodermal sinus tumors, in certain teratocarcinomas, and in certain gastrointestinal tumors. Liver-specific expression of AFP and ALB is the result of interactions of the regulatory sequences of their genes with trans-activating, transcriptional factors found in nuclear extracts from liver.

The methods of this invention may be used to control the expression of heterologous genes in tissue culture. This may be important where high levels of transcription of the heterologous genes are undesirable, because large concentrations of the heterologous protein within the cell leads to cell death. Further, where it is desired to express genes in normal liver cells, those genes may be linked to AFP regulatory regions with the silencer region deleted to thereby allow the expression of that heterologous gene in all liver cells. While other promoters may be useful for this purpose, the AFP promoter and enhancer are preferred because the AFP promoter is a strong promoter with a high level of transcriptional activity. Since the AFP regulatory elements are assembled in such a manner as to permit the expression of a linked gene in liver, inborn errors of metabolism due to the lack or abnormality of a gene may be corrected by the present invention. Such inborn errors include phenylketonuria, urea cycle disorders, hemophiliacs, $\alpha_1$-antitrypsin deficiency, and mucopolysaccharide deficiency. Furthermore, this method should be useful for treating viral hepatitis, such as caused by hepatitis C virus, by introducing the gene encoding interferon which has been shown to be highly effective against HCV.

The methods of the present invention may also be useful in the treatment of hepatocellular cancer. It has been shown by the inventors that is possible to arrest the growth of, or kill, mammalian carcinoma cells with a recombinant expression fragment comprising a AFP transcriptional regulatory sequences linked to a toxin gene. This recombinant expression vector may be incorporated into an infective virion. Upon administration of an infective virion containing the recombinant expression fragment to a patient, the toxin is selectively expressed in the target cell. It has been found that the level of expression of the toxin will vary depending on the type of cancer cell. By the methods of the present invention, it is possible to adjust the level of expression of the toxin in the cells. The control of expression may be advantageous to prevent necrosis of liver tissue in the patient or alternatively, to increase the rate of cell death for cancer cells which do not express large amount of AFP protein.

In mammalian cells, certain genes are ubiquitously expressed. Most genes, however, are expressed in a temporal and/or tissue-specific manner, or are activated in response to an extracellular inducer. For example, certain genes are actively transcribed only at very precise times in ontogeny in specific cell types or in response to some inducing stimulus. This regulation is mediated in part by the interaction between transcriptional regulatory sequences (which are for example promoter and enhancer regulatory DNA sequences), and sequence-specific, DNA-binding transcriptional protein factors.

In mammalian cells, normally two DNA sequences are required for the complete and efficient transcriptional regulation of genes that encode messenger RNA's in mammalian cells: promoters and enhancers. "Promoters" are located immediately upstream (5') from the start site of transcription. Promoter sequences are required for accurate and efficient initiation of transcription. A typical promoter includes an AT-rich region called a TATA box (which is located approximately 30 base pairs 5' from the start site of transcription initiation start site).

The activity of promoter sequences are modulated by other sequences called "enhancers". The "enhancer" sequence may be a great distance from the promoter in either an upstream, (5') or downstream (3') position. Hence, enhancers operate in an orientation- and position-independent manner. However, based on similar structural organization and function that may be interchanged the absolute distinction between promoters and enhancers is somewhat arbitrary. Enhancers increase the rate of transcription from the promoter sequence. It is predominantly the interaction between sequence-specific transcriptional factors with the promoter and enhancer sequences that enable mammalian cells to achieve tissue-specific gene expression. The presence of these transcriptional protein factors (tissue-specific, trans-activating factors) bound to the promoter and enhancers (cis-acting, regulatory sequences) enable other components of the transcriptional machinery, including RNA polymerase, to initiate transcription with tissue-specific selectivity and accuracy.

The "silencer" is a DNA region which inhibits transcription initiation by interfering with enhancer activity.

The term "functionally linked" as used herein means that the transcription regulatory region is linked to the heterologous gene in such a manner that the expression of the heterologous gene is controlled by the transcription regulatory region.

The term "transcription regulatory region" as used herein includes all of the sequences involved in the transcription of a gene including enhancers, silencers and promoters.

Similar to the regulatory structure of the ALB gene, the regulatory elements of the AFP genes promote tissue-specific expression in certain liver pathologies, such as HCC (Mol. Cell. Biol. 6: 477–487 (1988); Science 235: 53–58 (1987). The regulatory elements of a mammalian AFP gene consist of a specific 5' promoter-proximal region (located in some mammalian species between 85 and 52 bp 5' to the gene). This sequence is essential for transcription in hepatomas. In addition, there are upstream (5') regulatory elements well defined for the murine AFP gene which behave as classical enhancers (Mol. Cel. Biol. 6: 477–487 (1986); Science 235: 53–58 (1987). These upstream regulatory elements are designated elements I, II and III and are located between 1,000 to 7,600 bp 5" to the transcription initiation site for the murine AFP gene. These three enhancer domains are not functionally equivalent at generating tissue-specific expression of AFP. Elements I and II have the greatest capacity to direct liver-specific expression of AFP. It is important to note that the regulatory sequences of the AFP gene advantageously contain the sequences not only for tissue-specific transcriptional activation but also for repression of expression in tissues which should not express AFP.

The regulatory regions of the human AFP gene have been characterized. A structural gene placed in the correct orientation 3' to the wild-type AFP regulatory sequences will enable that structural gene to be selectively expressed in fetal liver, hepatomas, non seminomatous carcinomas of the testis, certain teratocarcinomas, certain gastrointestinal tumors and other normal and pathological tissues which specifically express AFP. The DNA fragment containing the transcriptional regulatory region of the AFP gene, which is a part of the recombinant DNA of the present invention, should be a DNA fragment obtained from the regulatory region of the AFP gene, that is, the 5'-flanking region (the upstream region) of the AFP gene.

As used herein the term "AFP promoter" means a promoter from a mammalian AFP gene region. Preferably the promoter is from the human AFP gene region. More preferably the promoter comprises the sequence disclosed in FIG. 13 (SEQ ID NOS:4,5,13 and 14). The promoter may be the wild-type promoter or it may be a mutated promoter. As used herein the term "AFP enhancer" means a DNA sequence encoding an enhancer from a mammalian AFP gene region. Preferably the enhancer is from the human AFP gene region. More preferably the enhancer comprises the sequences of domain A or domain B as disclosed in FIG. 14 (SEQ ID NOS:15–24). The enhancer may be the wild-type enhancer or a mutated enhancer. As used herein the term "AFP silencer" means a DNA sequence encoding a mammalian AFP silencer. Preferably the silencer is from the human AFP gene region. More preferably the silencer comprises the DNA sequence as disclosed in FIG. 5 (SEQ ID NOS:6 and 7). The silencer may be the wild-type silencer or a mutated silencer. The silencer may be the distal silencer or the proximal silencer.

The above-described transcriptional regulatory DNA fragment may be either a native 5'-flanking sequence of the AFP gene or a recombinant DNA fragment containing one or more of the enhancer, silencer and promoter of the AFP gene. The native 5'-flanking non-coding region of the AFP gene contains two enhancer sites, two silencer sites and one promoter site, as shown in FIG. 10, whereas the recombinant DNA fragment may have variable numbers of enhancer and silencer elements.

Further, as shown in FIG. 10, the native AFP gene has a glucocorticoid responsive element (g) in the transcriptional regulatory region. Under the presence of glucocorticoid, the responsive element modifies the expression of AFP. Therefore, when a recombinant DNA fragment containing the glucocorticoid responsive element is used the expression of a cancer-cell damaging protein can be regulated by administering glucocorticoid.

The toxin gene may be a DNA fragment encoding a substance which alters, damages or kills not only cancer cells but also normal cells. Because, as described above, the expression of the gene in the recombinant DNA construct of the present invention is controlled by the transcriptional regulatory region of the AFP gene, the DNA fragment encoding for such a substance can be controlled such that it is transcribed only in AFP-producing cancer cells. Such genes may encode for direct toxins or indirect toxins. Examples of "direct toxins" are toxin genes, such as diphtheria toxin (Maxwell, I. H., et al., Cancer Res., 46:4660–4664 (1986)) and ricin [Weiner, L. M., et al., 1989, Masui, H., et al., 1989]; cytokine genes [Blankenstein, T., et al., J. Exp. Med., 173, 1047–1052 (1991), Colombo, M. P., et al., J. Exp. Med., 173, 889–897 (1991), Leone, A., et al., Cell, 65, 25–35 (1991)]; tumor suppressor genes (Huang, M. J. S., et al., Science, 242, 1563–1566 (1988), Mercer, W. E., et al., Proc. Natl. Acad. Sci. USA, 88, 1958–1962 (1988)]; tumor vaccination genes, [Wallich, R., et al., Nature, 315, 301–305 (1985), Rollins, B., et al., Mol. Cell. Biol., 11, 3125–3131 (1991)] DNA sequences that yield anti-sense RNA to oncogenes; genes encoding tumoroidal substances JE/McP-1; genes that produce anti-virus substances; and genes that induce apoptosis.

Preferably, the direct toxin is diphtheria toxin (DT). This toxin catalyzes the transfer of the ADP-ribose moiety of NAD to elongation factor 2 (EF-2) thereby blocking protein synthesis and causing cell death. DT consists of 535 amino acids comprising two subunits designated the A and B chains (see FIG. 15A). The A chain (DT-A) which comprises the 193 amino-terminal residues catalyzes ADP-ribosylation of EF-2 and the B chain (DT-B) which comprises the 342 carboxyl terminal residues (SEQ ID NO:27) promotes the binding of the toxin to cells and the entry of DT-A into the cytosolic compartment. DT-A is extremely toxic once inside the cell and there is evidence that the introduction of a single molecule of this protein is lethal for a cell. (Yamaizumi et al. 1978)

More preferably, an attenuated form of the DT-A gene will be used in this invention. For example, an attenuated form of DT-A (tox 176) has been generated through chemical mutagenesis of the wild-type DT-A gene (SEQ ID NO:29) (Uchida et al. 1973; Yamaizumi et al. 1978) (see FIG. 15B). The mutant toxin has been shown to be about 30-fold less toxic than the wild-type protein. Such attenuated forms of toxin may enhance target cell specificity and prove to be highly versatile and effective agents for targeted cell killing.

Both the wild-type and mutant DT-A genes have been cloned and sequenced (Greenfield et al. (1983); PNAS 80: 6853–6857). They differ in the second position of codon 128, resulting in the substitution of aspartic acid for a glycine in the deduced amino acid sequence. Several inactive DT-A mutants have also been isolated (Giannini et al. 1984; Kaczorek et al., 1983). These studies have revealed amino acid residues critical for biological functions of DT-A. Knowledge of the relationship between sequence changes and diminished DT-A activity can be used by one skilled in the art to generate additional DT-A mutants with varying degrees of cytotoxicity. One skilled in the art, given the disclosure of this application, could generate recombinant DNA constructs for expression of the mutant toxin in cancer cells.

Alternatively an indirect toxin or enzyme pro-drug combinations may also be used; providing the enzyme is capable of selectively activating the administered compound either directly or through an intermediate to a cytostatic or cytotoxic metabolite. Equally the choice of compound will depend on the enzyme system used, but must be selectively metabolized by the enzyme either directly or indirectly to a cytotoxic or cytostatic metabolite. One skilled in the art could select such a compound.

The varicella zoster virus (VZV) encodes a specific thymidine kinase protein. The gene has been cloned, sequenced and characterized (J. Gen. Virol. 67: 1759–1816)). The VZV thymidine kinase will, in contrast to the mammalian enzyme, selectively monophosphorylate specific purine arabinosides and substituted pyrimidine compounds. 9-(β-D-arabinofuranosyl)- 6methoxy-9 H -purine is converted to 9-β-D-arabinofuranosyl adenine tripohosphate [Ara ATP] by this enzyme. [European Patent Application No. 0 415 731 which is incorporated by reference herein].

Other enzyme pro-drug combinations include the bacterial (for example from Pseudomonas) enzyme carboxypeptidase G2 with the pro-drug para-N-bis (2-chloroethyl) aminobenzoyl glutamic acid. Cleavage of the glutamic acid moiety from this compound releases a toxic benzoic acid mustard; alkaline phosphatase from, for example, calf intestine, will convert inactive phosphorylated compounds such as etoposide-phosphate, doxorubicin-phosphate, mitomycin phosphate, to toxic dephosphorylated metabolites. Penicillin-V amidase will convert phenoxyacetamide derivatives of doxorubicin and melphalan to toxic metabolites and the fungal (for example from Fusarium oxysporum) cytosine deaminase will convert 5-fluoroctosine to toxic 5-fluorouracil.

The heterologous gene for expression in mammalian cells may be any gene capable of being expressed in mammalian cells. For example, the gene may be phenylalanine hydroxylase, urea cycle enzymes, clotting factors, $\alpha_1$-antitrypsin, mucopolysaccharide or interferon.

The vector carrying such a recombinant DNA should be able to enter human cells and have no adverse effect on human normal cells. Examples of the vector are: plasmid vectors, retroviralvectors, and adenoviralvectors.

A variety of methods are available to introduce foreign genes into mammalian cells in vitro. The most popular techniques are the calcium phosphate precipitation method (Graham and van der Eb, 1973), DEAE-dextran-mediated transfection (Lopata et al. 1984), liposome mediated transfection (Cudd 1984) and electroporation (Potter et al. 1984). In the calcium phosphate precipitation procedure, DNA is coprecipitated with calcium phosphate to form insoluble particles which are taken up by cells by phagocytosis.

The DEAE-dextran protocol is a highly efficient and reproducible transfection procedure. A solution containing 2 mg/ml of the desired DNA, 250 mg/ml of DEAE-dextran (Mv500.000; Sigma), 50 mM Tris-HCl, pH 7.5, is filtered through 0.2µ filter and added to the culture medium. Following an incubation for 2 hours at 37° C., the medium is removed and the cells washed three times with medium and cultured in growth medium for 58 hours.

Liposome—mediated transfection is another transfection procedure. A solution containing 1 µg and 10 µl cationic liposomes (1 mg/ml) is added to 0.5 ml serum-free medium. This is applied to cells and incubated at 37° C. for 3 to 5 hours. The medium is then replaced with fresh growth medium and cultured for 48 hours.

Electroporation uses an electric field to open up pores in the cell which allow entry of DNA molecules presumably through diffusion (Fromm et al. 1985; Neumann et al. 1982; Wong and Neumann 1982). Electroporation is most conveniently done using suspension cultures, whereas the calcium phosphate precipitation method and the DEAE-dextran-mediated transfection are most easily done using monolayer cultures.

The technique of retroviral infection of cells to integrate artificial genes into mammalian cells in mammals employs retroviral shuttle vectors which are known in the art, (see for example Miller and Baltimore (1986) Mol. and Cell Biol. 6: 2895–2902). Essentially, retroviral shuttle vectors are generated using the DNA form of the retrovirus contained in a plasmid. These plasmids also contain sequences necessary for selection and growth in bacteria. Retroviral shuttle vectors are constructed using standard molecular biology techniques well known in the art. Retroviral shuttle vectors have the parental endogenous retroviral genes (eg. gag, pol and env) removed and the DNA sequence of interest inserted, such as the molecular chimaeras which have been described. They however, contain appropriate retroviral regulatory sequences for viral encapsidation, proviral insertion into the target genome, message splicing, termination and polyadenylation. Retroviral shuttle vectors can be derived from the Moloney murine leukemia virus (Mo-MLV) but it will be appreciated that other retroviruses can be used such as the closely related Moloney murine sarcoma virus. (European Patent Application No. 0 415 731 which is incorporated herein by reference). Certain DNA viruses may also prove to be useful as a delivery system. The bovine papilloma virus [BPV] replicates extrachromosomaly so that delivery system based on BPV have the advantage that the delivered gene is maintained in a nonintegrated manner.

The advantages of a retroviral-mediated gene transfer system are the high efficiency of the gene delivery to the targeted tissue, sequence specific integration regarding the viral genome (at the 5' and 3' long terminal repeat (LTR) sequences) and little rearrangements of delivered DNA compared to other DNA delivery systems.

Accordingly in one embodiment of the present invention there is provided a retroviral shuttle vector comprising a DNA sequence comprising a 5' viral LTR sequence, a cis acting psi encapsidation sequence, a recombinant DNA construct and a 3' viral LTR sequence.

In one embodiment, and to help eliminate non-tissue-specific expression of the molecular chimaera, the recombinant DNA construct may be placed in opposite transcriptional orientation to the 5' retroviral LTR. In addition, a dominant selectable marker gene may also be included which is transcriptionally driven from the 5' LTR sequence. Such a dominant selectable marker gene may be the bacterial neomycin-resistance gene NEO (Aminoglycoside 3" phosphotransferase type II), which confers on eukaroytic cells resistance to the neomycin analogue G418 sulphate (GENETICIN) The NEO gene aids in the selection of packaging cells which contain these sequences. Other vectors containing a NEO gene as a selectable marker have been described, for example, the N2 vector (Science 230: 1395–1398 (1985).

A theoretical problem associated with retroviral shuttle vectors is the potential of retroviral long terminal repeat (LTR) regulatory sequences transcriptionally activating a cellular oncogene at the site of integration in the host genome. This problem may be diminished by creating SIN vectors. SIN vectors are self-activating vectors which contain a deletion comprising the promoter and enhancer regions in the retroviral LTR. The LTR sequences of SIN vectors do not transcriptionally activate 5' or 3' genomic sequences. The transcriptional inactivation of the viral LTR sequences diminishes insertional activation of adjacent target cell DNA sequences and also aids in the selected expression of the delivered molecular chimaera. SIN vectors are created by removal of approximately 299 bp in the 3' viral LTR sequence (Biotechniques 4 504–512 (1986).

Thus preferably the retroviral shuttle vector of the present invention are SIN vectors.

Since the parental retroviral gag, pol and env genes have been removed from these shuttle vectors, a helper virus system may be utilized to provide the gag, pol and env retroviral gene products necessary to package or encapsidate the retroviral vector into an infective virion. This is accomplished by utilizing specialized "packaging" cell lines, which are capable of generating infectious, synthetic virus yet are deficient in the ability to produce any detectable wild-type virus. In this way the artificial synthetic virus contains a chimaera of the present invention packaged into synthetic artificial infectious virions free of wild-type helper virus. This is based on the fact that the helper virus that is stably integrated into the packaging cell contains the viral structural genes, but is lacking the psi site, a cis acting regulatory sequence which must be contained in the viral genomic RNA molecule for it to be encapsidated into an infectious viral particle.

In addition to removal of the psi site, additional alterations can be made to the helper virus LTR regulatory sequences to insure that the helper virus is not packaged in virions and is blocked at the level of reverse transcription and viral integration.

Selectivity of expression may be additionally improved by selective infection of liver cells. The retroviral env gene present in the packaging cell line defines the specificity for host infection. The env gene used in constructing the packaging cell line is modified to generate artificial, infective virions that selectively infect hepatocytes. As an example, a retroviral env gene introduced into the packaging cell may be modified in such a way that the artificial, infective virion's envelope glycoprotein selectively infects hepatocytes via the specific receptor mediated binding utilized by the hepatitis B virus (HBV).

HBV primarily infects hepatocytes via specific receptor mediated binding. The HBV proteins encoded by the pre-S1 and pre-S2 sequences play a major role in the attachment of HBV to hepatocytes (Hepadna Viruses edited Robinson et al. 189–203, 205–221, 1987). The env gene of the packaging cell is modified to include the hepatocyte binding site of the large S HBCV envelope protein. Such modifications of the env gene introduced into the packaging cell may be performed by standard molecular biology techniques well known in the art and will facilitate viral uptake in the target tissue.

The infective virion according to the invention may be formulated by techniques well known in the art and may be presented as a formulation with a pharmaceutically acceptable carrier therefore. Pharmaceutical acceptable carriers, in this instance, may comprise a liquid medium suitable for use as a vehicle to introduce the infective virion into the patient. An example of such a carrier is saline. The infective virion may be a solution or suspension in such a vehicle. Stabilizers and antioxidants and/or other excipients may also be present in such pharmaceutical formulations which may be administered by intra-venous or intra-arterial infusion. In the case of treating HCC intra-hepatic arterial infusion may be advantageous.

The amounts and precise regime in treating a mammal, will of course be the responsibility of the attendant physician, and will depend on a number of factors including the type and severity of the condition to be treated. However, for HCC, an intrahepatic arterial infusion of the artificial infective virion at the titre of between $2 \times 10^5$ and $2 \times 10^7$ colony forming units per ml (CFU/ml) infective virions is likely to be suitable for a typical tumor. Total amount of virions infused will be dependent on tumor size and would probably be given in divided doses.

Where the heterologous gene encodes for a metabolic enzyme, a metabolite must also be administered to the mammal. The dose of the drug will advantageously be in the range 0.1 to 250 mg per kilogram body weight of recipient per day, preferably 0.1 to 100 mg per kilogram body weight.

One skilled in the art could determine the dosage to be administered based on a number of factors, including the metabolic enzyme contemplated.

The term "substantially complete kill" means that the number of viable cells has been reduced by a 1 log reduction, for example, from $10^4$ to $10^3$ cells. More preferably, the number of viable cells has been reduced by 2 logs. Even more preferably, it has been reduced by 3 logs.

The following examples serve to illustrate the present invention but should not be construed as a limitation thereof:

EXAMPLE 1

HuH-7 is a human hepatoma cell line producing AFP which was obtained from Dr. J. Sato, Okayama University, Japan. (Nakabayashi et al., (1982) Cancer Res. 22:3858). HuH-7 was cultured in a chemically defined medium ISE-RPMI, which contains ethanolamine (30 μg/ml) in IS-RPMI. huH-1/cl-2 is a clone isolated from the parental huH-1 human hepatoma cell line (Huh and Utakoji (1981) Gann 72:178–179). It was obtained from Dr. Huh, University of Tokyo, Japan and was cultured in ISE-RPMI with 1% fetal calf serum. HeLa is a human cell line (Gey, (1952) Cancer Res. 12:264) which does not produce AFP. Hela cells were cultured in ISE-RPMI with 5% fetal calf serum. COS 7 cells are an african green monkey kidney cell line which does not produce AFP. The COS 7 cells were obtained from ATCC and were cultured in ISE-RPMI with 5% fetal calf serum.

In all cases, transfection was performed by the calcium phosphate precipitation method as described by Nakabayachi et al. (1989) J. Biol. Chem. 204: 266–271. In order to determine CAT activity, the transfected cells were lysed by several cycles of freezing and thawing and centrifuged at 15,000 rpm for 5 min. The supernatant was heated at 60° C. for 10 min. and analyzed for chloramphenicol acetyltransferase (CAT) activity according to Gorman et al. (1982) Mol. Cell. Biol. 2:1044. This heat treatment is essential for the detection of CAT activity in huH-1/cl-2 cells. Similar heat treatment of extracts resulted in a 3.5 fold increase in HuH-7 cell CAT activity.

pBR-CAT was constructed by inserting the HindIII-BamHI fragment obtained from pSV0-CAT obtained from Dr. B. Howard, (NCI/NIH) (Gorman et al. (1982) Mol. Cell Biol. 2:1044) into pBR322 purchased from BRL, Gaithersburg Md. according to the method of Walker et al., (1983) Nature 306:557. This plasmid contains the CAT coding sequence and the SV40 polyadenlyation signal but lacks the SV40 enhancer and early promoter elements.

CAT fusion genes were constructed by linking the CAT gene to AFP 5'-flanking sequences obtained by restriction enzyme digestion or polymerase chain reaction and inserting them into the HindIII site of pBR-CAT.

Specifically, pAF1.0-CAT was constructed by inserting the 980 bp sequence between −951 and +29 relative to the cap site of the human AFP gene into the HindIII site at the 5' end of the CAT gene of pBR-CAT.

To construct pAF5.1-CAT containing the 5.1 kb of the AFP 5'-flanking sequence, pAF1.0-CAT was digested completely with PstI, partially with EcoRI and a 5.7 kb DNA sequence containing a 0.9 kb EcoRI-HindIII human AFP DNA fragment (−870 to +29), the CAT gene and the pBR322 replication origin was recovered. pHAL-2w-Eco4.2, (a clone containing 4.2 kb AFP DNA from −5.1 to −871 bp inserted at the EcoRI site of pBR322) was digested completely with PstI and partially with EcoRI. A 4.9 kb DNA fragment consisting of the 4.2 kb AFP EcoRI DNA and the 748 bp PstI-EcoRI DNA fragment of pBR322 was isolated and ligated to the 5.7 kb DNA derived from pAF1.0-CAT.

EXAMPLE 2

Expression of CAT gene driven by the AFP 5'-flanking DNA region in HuH-7 and huH-1/cl-2 cells To determine whether the differences in AFP production in HuH-7 and huH-1/cl-2 cells are due to differences in transcriptional regulatory activities of the AFP 5'-flanking regions, the cells were transfected with plasmids containing the CAT gene to which various lengths of AFP 5'-flanking sequences were linked. Transfection and analysis of CAT activity were performed as described in Example 1. The results of the test are shown in FIGS. 1A and 1B. The amounts of cell extract used and the incubation times were 25 μg and 20 minutes for HuH-7 (lanes 1–5) and 100 μg and 180 minutes for huH-1/cl-2 (lanes 6–10).

The 5.1 kb AFP 5'-flanking DNA which contains the full AFP enhancer region (−4.9/−3.9 kb) supported a high level of CAT expression in HuH-7 (FIG. 1B, lane 3) but only a low level of expression in huH-1/cl-2 (FIG. 1B, lane 8). CAT expression support by the 1.0 kb AFP promoter region was also greater in HuH-7 than in huH-1/cl-2 (FIG. 1B, lanes 4 and 9). Thus there is a correlation between transcriptional activities of the AFP 5'-flanking sequences and the levels of AFP production in HuH-7 and huH-1/cl-2, respectively.

Comparison of CAT activities supported by 5.1 kb (containing the AFP enhancer) and 1.0 kb (without the AFP enhancer) of the AFP 5'-flanking sequence showed that the AFP enhancer stimulated the AFP promoter activity 25-fold in HuH-7 (FIG. 1B, lanes 3 and 4) but only 2-fold in huH-1/cl-2 (FIG. 1B, lanes 8 and 9). These results indicate that in huH-1/cl-2 cells the AFP enhancer does not stimulate the AFP promoter as much as in HuH-7 cells.

EXAMPLE 3

Analysis of AFP promoter and enhancer activities in HuH-7 and huH-1/cl-2 cells To show that enhancer activation of the AFP promoter is selectively inhibited in huH-1/cl-2 cells as suggested above, it is important to establish that both the AFP enhancer and the promoter are active in this cell line.

To analyze the functionality of the AFP promoter, the effect of dexamethasone was tested on the AFP promoter activity. This test is based on the observation that dexamethasone stimulates the AFP promoter only when it is functional. (Nakabayashi et al., (1989) J. Biol. Chem. 264:266) HuH-7 and huH-1/cl-2 cells were transfected with pAF1.0CAT incubated with or without $3 \times 10^{-6}$M dexamethasone for 2 days and analyzed for CAT activity. The amounts of extract and the incubation times were 25 μg and 20 min. for HuH-7 cells (lanes 1 and 2) and 100 μg and 180 minutes for huH-1/cl-2 cells (lanes 3 and 4). See FIG. 1C.

It was found that dexamethasone stimulated CAT activity supported by the 1.0 kb AFP promoter 9-fold in huH-1/cl-2 and 12-fold in HuH-7 cells. This result indicates that the AFP promoter is functional in huH-1/cl-2 cells.

Next the activity of the AFP enhancer was determined in HuH-7 and huH-1/cl-2 cells. The 2.4 kb full enhancer region (−5.3/−2.9 kb) and two subregions, 0.3 kb domain A (−4.0/−3.7 kb) and 0.4 kb domain B (−3.7/−3.3 kb) were individually tested in conjunction with SV40 promoter.

To construct pSV1'-CAT, the plasmid pSV2-CAT was digested with AccI and SphI and the smaller fragment was removed. The remaining DNA was made blunt-ended by treatment with the large fragment of DNA polymerase I and ligated through BglII linkers. This plasmid contains only 30% of one SV40 72 bp repeat sequence and the TATA box.

pSVAF2.4-CAT was constructed by inserting the 2.4 kb BglII-BglII fragment between −5.3 and −2.9 kb of the AFP gene prepared from λHAL- 2W into the BglII site of pSV1'-CAT. The plasmid λHAL-2W was described in Urano et al. (1984) Gene 32:255–261.

pSVAF0.4-CAT was constructed by inserting the 408 bp HindII-HaeIII fragment between −3.7 and −3.3 kb of the AFP gene which had been blunt-ended into the BglII site of pSV1'-CAT.

pSVAF0.3-CAT was constructed by digesting PSVAF2.9-CAT with BglII. The released 2.4-kb full enhancer fragment was digested with DraI and HindIII to release the 318-bp fragment. The HindIII end of this fragment was converted to blunt end, BglII liners were attached to both ends and the fragment was inserted into the BglII site of pSV1'-CAT.

All of these enhancer regions stimulated the SV40 promoter activity to essentially the same degrees in HuH-7 and huH-1/cl-2 cells. See Table 1.

TABLE 1

Expression of CAT activity from Various AFT-CAT fusion genes.

| Cell line | pSV2-CAT pmol/h/ μg of protein | % | pSVAF-2,4-CAT % | pSVAF-0,3-CAT % | pSVAF-0,4-CAT % | pSV1'-CAT % |
|---|---|---|---|---|---|---|
| HuH-7 | 731 | 100 | 62 (44) | 22 (16) | 5.9 (4) | 1.4 (1) |
| huH-1/cl-2 | 46 | 100 | 68 (38) | 25 (14) | 7.2 (4) | 1.8 (1) |
| HeLa | 32 | 100 | 3.5 (1.7) | 3.4 (1.6) | 3.2 (1.5) | 2.1 (1) |

This finding indicates that the AFP enhancer elements are as active in huH-1/cl-2 cells as in HuH-7 cells. These results suggest that positive transcription factors regulating the AFP enhancer and promoter are not limiting in huH-1/cl-2 cells.

EXAMPLE 4

Negative control elements suppress AFP enhancer activity in huH-1/cl-2 cells The examples described above supported the view that the AFP enhancer is unable to stimulate the promoter in huH-1.cl-2 cells. To test whether this is due to the action of negative regulatory elements located between the enhancer and the promoter, various lengths of DNA downstream of the enhancer (at −2.9 kb) of the 5.1 kb AFP 5'-flanking sequence in pAF5.1-CAT were deleted. (FIG. 2) To achieve the different deletions, the plasmid pAF5.1-CAT was digested completely with BglII and with SacI or BstNI or partially with HindIII. The SacI or BstNI or HindIII sites were blunt ended with Klenow fragment and ligated to BglII linkers. The plasmid was then religated. These deletions had little effect on CAT expression in HuH-7. In huH-1/cl-2, on the other hand, CAT expression changed with several deletions. In particular, significant increases were observed with deletions from −2.9 kb to −951 bp ([Δ2.0] in FIG. 2) (3.6 fold) and from −2.9 kb to −169 bp ([Δ2.7] in FIG. 2) (10-fold). These results suggest that at least two negative control regions exist between −1822 and −169 bp; one from −1822 to −951 (distal silencer "Sd") and the other from −402 to −169 bp (proximal silencer "Sp"). In addition, a small but consistent increase in CAT activity was observed associated with the deletion from −951 to −402 bp ([Δ2.5] in FIG. 2) which may suggest the presence of a third, weak negative control element in this region.

The 875-bp Sd region was analyzed for transcription-suppressive activity by inserting it back into pAF5.1[Δ2.7]-CAT in which a 2.7 kb sequence from −2.9 to −169 bp had been deleted. The Sd DNA was cut from the AFP region with HindIII and blunt ended with Klenow fragment. BglII linkers were ligated to the 875-bp fragment and the fragment was inserted into the BglII site in the plasmid pAF5.1[Δ2.7]-CAT. The resultant construct ([Δ2.7]+875) showed a five-fold lower CAT activity than the parental plasmid [Δ2.7] in huH-1/cl-2 cells (FIG. 2). To further delimit the silencer activity, the 875 bp DNA fragment was divided into two fragments by digestion with DraI enzyme to obtain a 409 bp 5'-fragment (from −1822 to −1414) and a 389 bp 3' fragment (from −1336 to −948), and each fragment was tested separately for suppressive CAT activity. The 409 bp 5' fragment ([Δ2.7]+409) suppressed CAT activity strongly, whereas the 3' fragment ([Δ2.7]+389) did so weakly (FIG. 2). This finding indicates that the major silencer activity is contained in the 409 bp 5' fragment. In the absence of the enhancer, the 5' fragment weakly stimulated AFP promoter activity. These results indicate that the action of Sd is to interfere with the AFP enhancer activity without affecting AFP promoter activity.

In the absence of the entire suppressor region ([Δ2.7]), the CAT activity expressed in huH-1/cl-2 is four fold lower than that in HuH-7 (25.9 versus 116). This finding suggests that another mechanism exists in huH-1/cl-2 to suppress the intrinsic AFP promoter activity, although this accounts only partially for the large difference in AFP production between HuH-7 and huH-1/cl-2.

EXAMPLE 5

The Sd element suppresses SV40 enhancer activity in a position-dependent manner

The effect of the Sd region on a heterologous enhancer was examined by inserting the 875 bp Sd region (from −1822 to −948 bp) into the BglII site in the SV40 enhancer of pSV1.6-CAT (SphI site converted to BglII site) in normal (d) and reverse orientations (e) (FIG. 3A). The resultant constructs expressed much lower CAT activity in huH-1/cl-2 cells than did the parental plasmid, indicating that Sd can suppress the heterologous SV40 enhancer in an orientation-independent manner. Suppression of CAT activity was also observed in HuH-7 and Hela cells although to much lesser extents. This finding suggests that the Sd activity is not strictly cell type specific. To show that the observed effects are not due to the disruption of the SV40 enhancer, a 924 bp DNA (from −4.9 to −4.0 kb) of the AFP gene with no known regulatory activity was inserted at the BglII site of pSV1.6-CAT as a control (c) (FIG. 3B). No significant changes in CAT expression were observed with the 924 bp DNA insert as compared to pSV1.6-CAT.

The orientation-independent suppression was also observed with the 409 bp Sd fragment in the SV40 enhancer. The 409 bp fragment (from −1822 to −1414 bp) was inserted into the AccI (a and b), BglII (f and g) or BamHI (h and i) site in normal and reverse orientations. When it was inserted upstream of the SV40 enhancer or downstream of the CAT gene, no suppression effect was observed in either orientation in any of the cell lines tested. These results show that the effect of Sd is orientation independent but position dependent.

EXAMPLE 6

Identification of a silencer element

To delimit the Sd region that exerts transcriptional suppression, we inserted various lengths of Sd subfragments in the SV40 enhancer (BglII site) of pSV1.6-CAT (FIG. 4). The longest fragment is a HindIII fragment of 875 bp. This fragment was blunt ended and BglII linkers were attached and the fragment was inserted into the BglII site of the SV40 enhancer. In addition, two sub-fragments from the 875 bp HindIII fragment were obtained by digesting the fragment with DraI and blunt ended. BglII linkers were attached and the fragments were inserted into the BglII site of the SV40 enhancer. The 31 bp fragment was synthesized by DNA Synthesis Laboratory, University of Calgary as two single strands of 31 bp and annealed these complementary strands to make double-stranded DNA. This was ligated into the BglII site of the SV40 enhancer.

Five fragments covering the region upstream of −1760 suppressed CAT activity. The shortest active fragment was 31 bp long, from −1790 to −1760. Four other fragments covering the region downstream of −1750 were inactive (FIG. 4). The 229-bp Sp region from −402 to −174 was also tested in a similar manner. It showed transcription-suppressive activity, although to a lesser degree than did Sd (FIG. 4).

We found that the 31-bp fragment which exhibited suppressive activity contains a 17-bp stretch, 5'-CTTCATAACTAATACTT-3', which is repeated four times within a 90-bp region from −1810 to −1720 (FIG. 5A (SEQ ID NO:6), underlined). A similar sequence is also found in the Sp region (FIG. 5B (SEQ ID NO:7), underlined). In all cases, the first six nucleotides, CTTCAT, and the last two, TT, are completely conserved (FIG. 5C). DNase I footprinting analysis by the method of Sawadaishi et al. (1988) Mol. Cell Biol. 8:5179–5187 showed that these sequences were protected by nuclear extracts prepared from huH-1/cl-2.

To further characterize the function of theses sequences, we inserted the 31-bp (SEQ ID NO:8) oligonucleotide (from −1790 to −1760 bp) into the BglII, AccI or BamHI site of pSV1.6-CAT. A mutant fragment with three-nucleotide substitutions was inserted into the BglII site (SEQ ID NO:9). The mutant sequence was synthesized. These constructs were transfected into huH-1/cl-2 or HuH-7 cells and 2 days later CAT activities were analyzed as described in Example 1. The amounts of extract and incubation times were 25 μg and 20 min. for HuH-7 (lanes 1 to 6) and 100 μg and 180 min. for huH-1/cl-2 (lanes 7 to 12). See FIG. 6, lanes 1 and 7, pSV1.6-CAT (positive control); 2 and 8, wild-type 31 bp fragment inserted in BglII; 3 and 9, mutant fragment inserted in BglII; 4 and 10, wild-type fragment inserted in AccI; 5 and 11, wild-type fragment inserted in BamHI; 6 and 12, pSV1'-CAT (negative control).

The fragment inserted within the SV40 enhancer strongly suppressed CAT activity in huH-1/cl-2 (FIG. 6A, lane 8), but only a weak suppression was observed in HuH-7 (FIG. 6A, lane 2). The insertion of the fragment upstream of the SV40 enhancer (FIG. 6A, lanes 4 and 10) or downstream of the CAT gene (FIG. 6A, lanes 5 and 11) had no effect on CAT activity in either cell line. Substitution of three nucleotides within the 17-bp repeated sequence (SEQ ID NO:9) (FIG. 6B) resulted in loss of suppressive activity (FIG. 6A, lane 9). This finding confirms the association of the suppressive activity with this sequence.

To determine the relationship between transcriptional suppression and the number of copies of the Sd elements, one, three, or eight copies of the 31-bp sequence (SEQ ID NO:8) was inserted into pAF5.1[Δ2.7]-CAT. The 31 bp synthetic fragment which has BglII sites on both ends was ligated into the BglII site of pAF5.1[Δ2.7]-CAT. In order to obtain multiple copies of the fragment, the 31 bp fragment was multimerized by self-ligation and then inserted into the BglII site of pAF5.1[Δ2.7]-CAT, which was then transfected into HuH-7 or huH-1/cl-2 cells. The level of CAT activity was measured by the method of Example 1 (see FIG. 6C). Analysis of CAT expression from these constructs showed that CAT activity decreased with increasing number of copies of this sequence in huH-1/cl-2 but not in HuH-7 (FIG. 6C). The CAT activities are expressed relative to that of pAF0.2-CAT.

EXAMPLE 7

Referring to FIG. 7, the diphtheria toxin gene, a known gene, codes for diphtheria toxin consisting of an A and B-chain. It is known that diphtheria toxin can kill eukaryotic cells by blocking protein synthesis. The B-chain is involved in the binding of the A-chain to a cell. The sequence of the A and B chain of the DT gene is published. [Greenfield, L., et al., Proc. Natl. Acad. Sci. USA, 80, 6853–6857 (1983)] See FIG. 15A (SEQ ID NOS:26 and 27). The DE-A gene and the tox-176 gene were obtained from Dr. Bernstein, Mount Sinai Hospital, Toronto. A DNA fragment coding for a modified A-chain (HToxin) was used. This modified DNA fragment was made by using PCR synthesis. This DNA fragment (HToxin) encodes for an A-chain having Cys as the 66th amino acid and Arg as the 194th amino acid, instead of the natural A-chain having Tyr and Pro, respectively, as reported by Greenfield and others. This DNA fragment was provided with a Hind III restriction enzyme cleavage site at the N-terminal and a HpaI restriction enzyme cleavage site at the C-terminal, using synthetic primers containing the HindIII or the HpaI site, respectively.

pSV2-CAT [obtained from Dr. B. H. Howard, NCI/NIH] [Gorman, et al.. Mo. Cell. Biol..2, 104 (1982)] was digested by Hind III and HpaI to remove the CAT gene, and the DNA fragment encoding the HToxin DNA was inserted into the plasmid to construct a recombinant plasmid pSV2/HToxin. This recombinant plasmid was used as a positive control because it is expressed nonspecifically in most cell lines under the direction of the SV40 early promoter.

The plasmid pTHX1 was obtained from Dr. Bernstein, Mount Sinai Hospital, Toronto. It contains a wild-type DT-A gene next to the metallothionein gene promoter.

The plasmid pTHX-176 contains a mutant DT-A gene having Asn instead of Gly in the 128th position from the N-terminus. This plasmid was obtained from Dr. A. Bernstein, Mount Sinai Hospital, Toronto.

The cell-killing effect of pSV2/HToxin was determined by comparing it with the cell-killing effects of other plasmids. More specifically, HuH-7 cells were transfected by the method of Example 1 with pSV2-CAT alone or with pTHX1, pTHI-176 or pSV2/HToxin. Then, the CAT activities expressed by these transfected cells were determined. The ability of a particular vector to suppress protein synthesis is indicated by the level of CAT activity. As the amount of protein synthesis is suppressed, the level of CAT activity decreases [Nakabayashi H., et al., Mol. Cell. Biol., 11(12), 5885–5893 (1991)]. The results, shown in FIG. 8, indicate that pTHX1 and pSV2/HToxin have substantially the same level of suppressing effect on the CAT activity and therefore substantially the same level of cell-killing effect. pTHI-176 exhibited a level of suppressing effect about one third of the level exhibited by pTHX1.

The results indicated that the AFP regulatory sequences used directed the expression of the HToxin gene in AFP producing hepatoma cells.

EXAMPLE 8

Effect of Diphtheria toxin on cell lines

The plasmid pSV2/HT/neo$^r$ was obtained by linking the neomycin resistant gene (neo$^r$ [Stratagene, La Jolla, Calif.] to the above-mentioned pSV/HToxin. The plasmid pSV2/HToxin was idgested with BamHI and then with the Klenow fragment to form blunt ends. pMCl-neo$^r$ (Stratagene, La Jolla Calif.) was treated with XhoI and SalI to release the neo$^r$ gene (1083 bp). This was inserted into the treated pSV2/HToxin plasmid above by blunt end ligation.

The plasmid pMC1-neo$^r$ was obtained from Stratagene, La Jolla, Calif.

HuH-7 cells and HeLa cells were transfected with pSV2/HT/neo$^r$ (see FIG. 9) or a control plasmid pMCl-neo$^r$ (Strategene) by the calcium phosphate method of Example 1. Transformants having neo$^r$ were selected by using G418 (GIBCO). Following transfection, cells were treated with 50 μg/ml of G418 for two days and then with increasing amounts (up to 200 μg/ml for HuH-7 cells and 1 mg/ml for HeLa cells) for 3–4 weeks. When the HeLa and HuH-7 cells were transfected with the control plasmid, pMCl-neo, both cell lines formed colonies of the transformants because the plasmid has the neo$^r$ gene. On the other hand, when the HeLa and HuH-7 cells were transfected with the plasmid pSV/HT/neo$^r$ which has the neo$^r$ gene, neither of the cell lines formed colonies because the plasmid pSV/HT/neo$^r$ also has HToxin gene expression, resulting in death of the transformants. Neither of the cell lines transfected with pUC19 (BRL), which does not contain either of the genes (i.e. a negative control) formed colonies (see Table 2). These results prove that the HToxin gene has a cell-killing effect in both HuH-7 and HeLa cells.

TABLE 2

| | Number of Colonies ($10^5$cells) | |
|---|---|---|
| Plasmid | HuH-7 | HeLa |
| pMClneo$^r$ | 4.2 | 0.5 |
| pSV2/HToxin/neo$^r$ | 0 | 0 |
| pUC19 | 0 | 0 |

EXAMPLE 9

Effect of the Silencer Region on the Cell-killing by Diphtheria Toxin

Various recombinant plasmids as shown in FIG. 10 were constructed by linking the HToxin gene to DNA chains containing different lengths of the transcriptional regulatory regions of the AFP gene. More specifically, the above-mentioned pSV2/HToxin was digested by Hind III and BamHI to obtain a DNA fragment having 759 bp which included the HToxin gene. The 759 bp DNA fragment was inserted in between the HindIII and BamHI sites of the pGEM-7Z vector (Promega), thus constructing pGEM7Z/HToxin. The plasmid pAF4.9/HToxin comprises the entire transcriptional regulatory region of the AFP gene, and the HToxin gene controlled by the transcriptional regulatory region.

The 4.9 kb 5'-flanking region of the AFP gene was obtained by partially digesting pAF5.1-CAT (Example 1)

with HindIII, electrophoresing the resultant fragments in a 0.4% agarose, then collecting the 4.9 kb DNA fragment. The collected fragment was inserted into the HindIII site of the above-mentioned pGEM72/HToxin, thus obtaining the desired plasmid, pAF4.9/HToxin. pAF4.9[Δ2.7]/HToxin in which the 4.9 kb 5'-flanking region of the AFP gene lacks a region from −2.9 kb to −169 bp, (i.e. the silencer region) was obtained by partially digesting pAF5.1[Δ2.7]-CAT with HindIII and inserting the resultant 2.2 kb DNA fragment into the Hind III site of pGEM/HToxin.

The plasmid pAF4.9[Δ2.7](S)$_8$/HToxin comprises the transcriptional regulatory region of the AFP gene and the HToxin gene controlled by the AFP enhancer, 8 copies of the AFP silencer element and the promoter. This was obtained by partially digesting pAF5.1[Δ2.7](S)$_8$-CAT (Example 6) with HindIII and inserting the 2.4 kb fragment having the enhancer and 8 copies of the silencer elements and the promoter into the HindIII site of pGEM/HToxin. pAF0.2/HToxin was obtained by the following steps: digestion of pAF4.9[Δ2.7]/HToxin by SmaI, ligation with a BglII linker, BglII digestion and removal of short fragments between the SmaI and BglII sites, and then BglII self-ligation. The plasmid pAF0.2/HToxin is a comparative example that lacks the enhancer and silencer sequences.

The plasmid pAF(AB)$_2$(S)$_8$/HToxin was generated by digesting pAF4.9[Δ2.7](S)$_8$/HToxin with EcoRI and inserting the 72.8-bp DraI-HaeIII fragment (−4.0/−3.3 kb) after attaching EcoRI linkers.

The plasmid pAF(AB)$_1$(S)$_8$/HToxin was generated by digesting pAF4.9[▷2.7](S)$_8$/HToxin with EcoRI and inserting two copies of the DraI-HaeIII fragment (−4.0/−3.3 kb) after attaching EcoRI linkers.

The plasmid pAF(A)$_3$(B)$_1$(S)$_8$/HToxin was generated by digesting pAF(AB)$_1$(S)$_8$/HToxin with XbaI inserting two copies of DraI-HindIII fragment (−4.0/−3.7 kb) after converting blunt ends and attaching XbaI linkers.

The plasmid pAF (A)$_3$(B)$_1$/HToxin was generated by removing 8 copies of silencer element from pAF(A)$_3$(B)$_1$(S)$_8$/HToxin by digestion with BglII followed by religation.

Two hepatoma cell lines (HuH-7, huH-1) and two non-hepatic cell lines (HeLa, COS) were transfected with the recombinant plasmids containing the HToxin gene together with pSV2-CAT. The cell-damaging effects expressed in the transfected cells were examined by determining the level of suppression of CAT expression caused by the HToxin expression by the methods of Example 1. HuH-7 cells were cultured in ISE-RPMI alone, huH-1/cl-2 cells were cultured in ISE-RPMI with 1% fetal calf serum. The non-hepatic cell lines were cultured in ISE-RPMI with 5% fetal calf serum. 0.5×10$^5$ cells/cm$^2$ of HeLa and COS7 [Gluzman, Y., Cell, 23, 175–182 (1981)] and 0.5×10$^5$ cells/cm$^2$ of HuH-7 and huH-1/cl-2 [Huh, N. and Utakoji, T., Gann, 72, 178–179 (1981)] were inoculated and transfected with 10 μg of pSV2/HToxin and various amounts of the above-described recombinant plasmids by the Ca$^{2+}$ precipitation method [Gorman et al., Mol. Cell. Biol., 2, 104 (1982)]. After 48 hours, the cells were collected and the CAT activities were determined. The results are shown in FIG. 11. As indicated in the figures, pSV2/HToxin strongly suppressed the CAT activity in all the cell lines, and pAF4.9/HToxin strongly suppressed the CAT activity in the AFP highly-producing hepatoma cell line HuH-7 (FIG. 11A) but did not suppress CAT activity in huH-1/cl-2 FIG. 11B) and the non-hepatic cell lines, HeLa (FIG. 11C) or COS7(FIG. 11D). pAF4.9 [Δ2.7]/HToxin, lacking the silencer region, suppressed the CAT activity in HuH-7 and huH-1/cl-2. On the other hand, pAF4.9[Δ2.7](S)$_8$/HToxin having 8 copies of silencer sequences suppressed the CAT activity in HuH-7 (FIG. 11A) but not in huH-1/cl-2 (FIG. 11b). pAF0.2/HToxin lacking the AFP transcriptional regulatory region except for 200 bp of the promoter region did not suppress the CAT activity in any of the cell lines.

The results show that the HToxin gene can be expressed selectively in AFP highly-producing hepatoma cells by using recombinant DNA according to the present invention, such as pAF4.9/HToxin and pAF4.9[Δ2.7](S)$_8$/HToxin.

The effect of increasing the number of AFP enhancers elements on the expression of the CAT gene was determined to be as follows.

|  | Relative CAT Activity | |
|---|---|---|
| AFP enhancer domain A | 1 copy | 6.8 |
|  | 3 copies | 52.4 |
| AFP enhancer domain B | 1 copy | 3.3 |
|  | 3 copies | 34.5 |

As described above, a recombinant DNA enters both normal and cancer cells but causes the expression of the linked gene selectively in AFP-producing cells. Therefore, the recombinant DNA of the present invention can be suitably used as a gene cancer-therapeutic agent which damages or kills AFP-producing cells, e.g. hepatocellular carcinoma, without adversely affecting normal cells.

EXAMPLE 10

Generation of single-base substitution mutations in the AFP promoter

To introduce single-base mutations in PE and MPE sequences, an oligonucleotide-directed in vitro mutagenesis system version 2 (Amersham) was used. This system was based on the method of Eckstein and coworkers (Taylor et al., 1985a; Taylor et al. 1985b; Nakamaye and Eckstein, 1986; Sayers et al., 1988). The procedure utilized single-stranded pBS-200 plasmid DNA as a template. This single-stranded DNA was hybridized to an oligonucleotide primer (spanning PE or MPE regions) harboring a mutation at the desired site. The primed single-stranded pBS-200 plasmid was then extended to form the complementary strand. Subsequently, the wild type strand was removed, and resynthesized using the mutant strand as template. For this purpose, eight oligonucleotides were synthesized (supplied by The Regional DNA Synthesis Laboratory, University of Calgary). To generate point mutations in PE, the following oligonucleotides were used as mutant primers: PE mutant I, PE mutant II, PE mutant III, PE mutant IV (see Table 3).

To generate point mutations in MPE, the following oligonucleotides were used as mutant primers: MPE mutant I, MPE mutant II, MPE mutant III, and MPE mutant IV (see Table 3). The mutated pBS-200 [PE and MPE] plasmids were introduced into E. coli XL-1Blue host bacteria. In order to obtain the correct mutations, pBS-200 plasmids prepared from 12 to 48 bacterial colonies were screened by single-lane sequencing. The correct mutants were further confirmed by sequencing the entire sequences.

TABLE 3

List of oligonucleotide primers used in this study

| Names | SEQ ID NO: | Sequences (5' to 3') |
|---|---|---|
| CAT | 30 | dCAACGGTGGTATATCCAGTG |
| AdML | 31 | dAGTCATGCCCGCTTTTGAGA |

TABLE 3-continued

List of oligonucleotide primers used in this study

| Names | SEQ ID NO: | Sequences (5' to 3') |
|---|---|---|
| γ-globin | 32 | dGTGATAGTAGCCTTGTCCTC |
| PE mutant I | 33 | dATGCTGTGAATTATTG |
| PE mutant II | 34 | dCTGTTAAGTATTGGCA |
| PE mutant III | 35 | dTTAATTATGGGCAAAT |
| PE mutant IV | 36 | dATTATTGGAAAATGTC |
| MPE mutant I | 37 | dCAAAAGGTGACTAGTT |
| MPE mutant II | 38 | dAGGTTACGAGTTAACA |
| MPE mutant III | 39 | dTTACTAGTGAACAGGC |
| MPE mutant IV | 40 | dCTAGTTAAAAGGCATT |
| Pr - 169 BglII | 41 | dGATCAGATCTTACAAATAACCGCTATGCTG |
| PR - 98 BglII | 42 | dGATCAGATCTTTTCAACCTAAGGAAATACC |
| KS | 43 | dCGAGGTCGACGGTATCG |
| SK | 44 | dTCTAGAACTAGTGGATC |
| T3 | 45 | dATTAACCCTCACTAAAG |
| t7 | 46 | dTAATACGACTCACTATAGGG |

This mutagenesis created plasmid PEII, MPEII and PEII, MPEII which are shown in FIG. 13 (SEQ ID NOS:4,5,13 and 14). The plasmids were transfected into HuH-7 cells by the methods of Example 1.

The level of promoter activity was measured by measuring the CAT activity by the methods of Example 1. The results show that all mutations resulted in decreased promoter activity, particularly MPEII.

EXAMPLE 11

Generation of single-dose substitution mutations in the AFP enhancer and silencer regions Wild-type and mutant enhancer and silencer elements were synthesized (FIG. 14, SEQ ID NOS:8,15 to 25) and inserted into the BglII site of pAF0.2-CAT. The resulting plasmids were transfected into HuH-7 cells by the methods of Example 1. The level of CAT activity was determined by the method of Example 1. The results indicate that the wild-type enhancer elements stimulated CAT expression in a highly dose-dependent manner, i.e., 3 copies of enhancer elements resulted in about a 10-fold increase in CAT expression over one copy of enhancer element. The mutant enhancer, on the other hand, showed much less stimulatory activity and dose dependency.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

References

The following references are cited in this application at the relevant portion of the application.

European Patent Application No. 0 415 731.

Behringer, R. R., Matthews, L. S., Palmiter, R. D. and Brinster, R. L. 1988. Dwarf mice produced by genetic ablation of growth hormone-expressing cells. Genes. Devel. 2, 453–461.

Berk. P. (ed) Seminars in Liver Disease 4 No. 2 Thieme Stratton Inc. New York, N.Y. (1984).

Blankenstein, T., Qin, Z., Uberla, K., Muller, W., Rosen, H., Volk, H. D., and Diamantstein, T. (1991). Tumor suppression after tumor cell-targeted tumor necrosis factorgene transfer. J. Exp. Med., 173, 1047–1052.

Breitman, M. L., Clapofe, S., Rosant, J., Tsui, L. C., Glode, M., Maxwell, I. H. and Bernstein A. 1987. Genetic ablation: Targeted expression of a toxin gene causes microphthalmia in transgenic mice. Science 238, 1563–1565.

Breitman, M. L., Rombola, H., Maxwell, I. H., Klintworth, G. K. and Bernstein, A. 1990. Genetic ablation in transgenic mice with an attenuated diphtheria toxin A Gene. Mol. Cell. Biol. 10, 474–479.

Colombo, M. P., Ferrari, G., Stoppacciaro, A., Parenza, M., Rodolfo, M., Mavillo, F., and Parmiani, G. (1991). Granulocyte colony-stimulating factor gene transfer suppresses tumorigenicity of a murine adenocarcinoma in vivo. J. Exp. Med., 173, 889–897.

Culver, K. W., Ram, Z., Wallbridge, S., Ishii, H., Oldfield, H. O., and Blaese, R. M. (1992). In vivo gene transfer with retroviral vector-producer cells for treatment of experimental brain tumors. Science, 256, 1550–1552.

Dubensky, T. W., Campbell, B. A., and Villarreal, L. P. (1984). Direct transfection of viral and plasmid DNA into the liver or spleen of mice. Proc. Natl. Acad. Sci. USA, 81, 7529–7533.

Ellis, J. and Bernstein, A. (1989). Gene targeting with retroviral vectors: Recombination by gene conversion into regions of nonhomology. Mol. Cell. Biol., 9, 1621–1627.

Felgner, P. L. and Rhodes, G. (1991). Gene therapeutics. Nature, 349, 351–352.

Gey, (1952) Cancer Res. 12:264.

Giannini, G., Rappuoli, R. and Ratti, G. 1984. The aminoacid sequence of two non-toxic mutants of diphtheria toxin: CRM45 and CRM197. Nucl. Acids Res. 12, 4063–4069.

Goring, et al. (1987) Science 235:456–458.

Gorman, et al. (1982) Mol. Cell. Biol. 2:1044.

Graham, F. and van der Eb, A. 1973. A new technique for the assay of infectivity of human adenovirus 5 DNA. Virology 52, 456–467.

Greenfield, L., Bjorn, M. J., Horn, G., Fong, D., Buck, G. A., Collier, R. J., and Kaplan, D. A. (1983). Nucleotide sequence of the structural gene for diphtheria toxin carried by corynebacteriophage β. Proc. Natl. Acad. Sci. USA, 80, 6853–6857.

Gutierrez, A. A., Lemoine, N. E., and Sikora, K. (1992). Gene therapy for cancer. Lancet, 339, 715–721.

Friedman, T. (1989). Progress toward human gene therapy. Science, 224, 1275–1281.

Huang, H. J. S., Yee, J. K., Shew, J. Y., et al. (1988). Suppression of the neoplastic phenotype by replacement of the RB gene in human cancer cells. Science, 242, 1563–1566.

Huber, B. E., Richards, C. A., and Krenitsky, T. A. (1991). Retroviral-mediated gene therapy for the treatment of hepatocellular carcinoma: An innovative approach for cancer therapy. Proc. Natl. Acad. Sci. USA, 88, 8039–8043.

Huh and Utakoji (1981) Gann 72:178–179.

Ingram, et al., (1981) PNAS 78:4694.

Kaczorek, M., Delpeyroux, F., Chenciner, N. Streeck, R. E. (1983). Nucleotide sequence and expression of the diphtheria tox228 gene in Escherichia coli. Science, 221, 855–858.

Kaneda, Y., Iwai, K., and Uchida, T. (1989). Increased expression of DNA cointroduced with nuclear protein in adult rat liver. Science, 243, 375–378.

Kuriyama, S., Yoshikawa, M., Ishizaka, S., Tsujii, T., Ikenaka, K., Kagawa, T., Morita, N., and Micoshiba, K. (1991). A potential approach for gene therapy targeting hepatoma using a liver-specific promoter on a retroviral vector. *Cell Struc. Func.* 16, 503–510.

Leone, A., Flatow, U., King, C. R., et al. (1991). Reduced tumour incidence metastatic potential and cyclokine responsiveness of nn23 transfected melanoma cells. *Cell,* 65, 25–35.

Lopata, M. A., Cleveland, D. W. and Sollner-Webb, B. 1984. High-Level expression of a chloramphenicol acetyltransferase gene by DEAE-dextran-mediated DNA transfection coupled with a dimethyl sulfoxide or glycerol shock treatment. *Nucl. Acids Res.* 12, 5707-.

Masui, H., Kamrath, H., Apell, G., Houston, L. L., and Mendelsohn, J. (1989). Cytotoxicity against human tumor cells mediated by the conjugate of anti-epiderman growth factor receptor monoclonal antibody to recombinant ricin A chain. *Cancer Res.,* 49, 3482–3488.

Maxwell, I. H., Maxwell, F., and Glode, L. M. (1986). Regulated expression of a diphtheria toxin-A-chain gene transfected into human cells: Possible strategy for inducing cancer cell suicide. *Cancer Res.,* 46, 4660–4664.

Maxwell, F., Maxwell, I. H., and Glode, L. M. (1987). Cloning, sequence, determination, and expression in transfected cells of the coding sequence for the tox 176 attenuated diphtheria toxin A chain. *Mol. Cell. Biol.,* 7, 1576–1579.

Mercer, W. E., Shields, M. T., Lin, D., Appella, E., Ulrich, S. J. (1991). Growth suppression induced by wild-type p53 protein is accompanied by selective down-regulation of proliferating-cell nuclear antigen expression. *Proc. Natl. Acad. Sci. USA,* 88, 1958–1962.

Miller, A. D. (1992). Human gene therapy comes of age. *Nature,* 337, 455–460.

Miller and Baltimore (1986) *Mol. and Cell. Biol.* 6:2895–2902.

Miyanohara, A., Sharkey, M. F., Witztum, J. L., Steinberg, D., and Friedmann, T. (1988). Efficient expression of retroviral vector-transduced human low density lipoprotein (LDL) receptor-deficient rabbit fibroblast in vitro. *Proc. Natl. Acad. Sci. USA,* 85, 6538–6542.

Nakabayashi, H., Taketa, K., Miyano, K., Yamane, T., and Sato, J. (1982). Growth of human hepatoma cells lines with differentiated functions in chemically defined medium., *Cancer Res.,* 42, 3858–3863.

Nakabayashi, H., Taketa, K., Yamane, T., Miyano, K., and Sato, J. (1984). Phenotypical stability of a human hepatoma cell line, HuH-7, in long-term culture with chemically defined medium. *Japan. J. Cancer Res.* (*Gann*), 75, 151–158.

Nakabayashi, H., Watanabe, K., Saito, A., Ohtsuru, A., Sawadaishi, K., and Tamaoki, T. (1989). Transcriptional regulation of α-fetoprotein expression by dexamethasone in human hepatoma cells. *J. Biol. Chem.,* 264, 266–271.

Nakabayashi, H., Hashimoto, T., Miyao, T., Tjong, T., Chan, J., and Tamaoki, T. (1991). A position-dependent silencer plays a major role in repressing α-fetoprotein expression in human hepatoma. *Mol. Cell. Biol.* 11, Nerenstone, et al., *Cancer Treatment Review,* 15 1–31 (1988).

Neumann, E., Schaefer-Rider, M., Wang, Y., and Hofschneider, P. H. 1982. Gene transfer into mouse lyoma cells by electroporation in high electric fields. *EMBO J.* 1, 841–845.

Otsuru, A., Nagataki, S., Koji, T. and Tamaoki, T. 1988. Analysis of alphafetoprotein gene expression in hepatocellular carcinoma and liver cirrhosis by in situ hybridization. *Cancer* 62, 1105–1112.

Palmiter, R. D., Behringer, R. R., Quaife, C. J., Maxwell, F., Maxwell, I. H. and Brinster, R. L. 1987. Cell lineage ablation in transgenic mice by cell-specific expression of a toxin gene. *Cell* 50, 435–443.

Pappenheimer, A. M. Jr. 1977. Diphtheria toxin. *Ann. Rev. Biochem.* 46, 69–94.

Potter, H., Weir, L. and Leder, P. 1984., Enhancer-dependent expression of human K immunoglobulin genes introduced into mouse pre-B lymphocytes by electroporation. *Proc. Natl. Acad. Sci. U.S.A.* 81 7161–7165.

Rollins, B. and Sunday, M. (1991). Suppression of tumour formation in vivo by expression of the JE gene in malignant cells. *Mol. Cell. Biol.,* 11, 3125–3131.

Rosenberg, S. A., Aebersold, P., Cometta, K., Sasid, A., Morgan, R., Moen, R., Karson, E. M., Lotze, M. T., Yang, J. C., Topalian, S. L., Merino, M. J., Culver, K., Miller, D., Blaese, R. M., Anderson, W. F. (1990). Gene transfer into humans-Immunotherapy of patients with advanced melanoma, using tumor-infiltrating lymphocytes modified by retroviral gene transduction. *N. Engl. J. Med.,* 323, 570–578.

Sawadaishi, K., Morinaga, T. and Tamaoki, T. 1988. Interaction of a hepatoma-specific nuclear factor with transcription-regulatory sequences of the human α-fetoprotein and albumin genes. *Mol. Cell. Biol.* 8, 5179–5187.

Thorpe, P. E., Wallace, P. M., Knowles, P. P., Relf, M. G., Brown, A. N. F., Watson G. J., Blakey, D. C., and Newell, D. R. (1988). Improved antitumor effects of immunotoxins prepared with deglycosylated ricin A-chain and hindered disulfide linkages. *Cancer Res.,* 48, 6396–6403.

Uchida, T., Pappenheimer, A. M. and Greany, R. 1973. Diphtheria toxin and related proteins. I. Isolation and properties of mutant proteins serologically related to diphtheria toxin. *J. Biol. Chem.* 2248, 3838–3844.

Urano, et al. (1984) *Gene* 32:255–261.

Wallich, R., Bulbuc, N., Hammerling, J., et al. (1985). Abregation of metastatic properties of tumour cells by de novo expression of H2K antigens following H2 gene transfection. *Nature,* 315, 301–305.

Watanabe, K., Saito, A. and Tamaoki, T. 1987. Cell-specific enhancer activity in a far upstream region of a human α-fetoprotein gene. *J. Biol. Chem.* 262, 4812–4818.

Weatherall, D. J. (1991). Gene therapy in perspective. *Nature,* 349, 255–276.

Wilson, J. M., Grossman, M., Wu, C. H., Chowdhury, N. R., Wu, G. Y., and Chowdhury, J. R. (1992). Hepatocyte-directed gene transfer in vivo leads to transient improvement of hypercholesterolemia in low density lipoprotein receptor-deficient rabbits. *J. Biol. Chem,* 267, 963–967.

Wilson, J. M., Grossman, M., Cabrera, J. A., Wu, C. H., and Wu G. Y. (1992). A novel mechanism for achieving transgene persistence in vivo after somatic gene transfer into hepatocytes. *J. Biol. Chem.,* 267, 11483–11489.

Wu, C. H., Wilson, J. M., and Wu, G. Y. (1989). Targeting genes: Delivery and persistent expression of a foreign gene driven by mammalian regulatory elements in vivo. J. Biol. Chem., 264, 16985–16987.

Yang, N-S, Burtkholder, J., Roberts, B., Martinell, B., and McCabe, D. (1990). In vivo and in vitro gene transfer to mammalian somatic cells by particle bombardment. 87, 9568–9572.

Wu, G. Y. and Wu, C. H. (1988). Receptor-mediated gene delivery and expression in vivo *J. Biol. Chem.* 263, 14621–14624.

Wu, G. Y. and Wu, C. H. (1988). Evidence for targeted gene delivery to Hep G2 Hepatoma cells in vitro. *Biochemistry*, 27, 887–892.

Wong, T. K. and Neumann, E. 1982. Electric field mediated gene transfer. *Biochem. Biophys. Res. Comm.* 107, 584–587.

Wu, G. Y., Wu, C. H. and Rubin, M. L. 1985. Acetaminophen hepatotoxicity and targeted rescue: A model for specific chemotherapy of hepatocellular carcinoma. *Hepatology* 5, 709–713.

Wu, G. Y. and Wu, C. H. 1987. Receptor-mediated in vitro gene transformation by a soluble DNA carrier system. *J. Biol. Chem.* 262, 4429–4432.

Yamaizumi, M., Mekada, E., Uchida, T. and Okada, Y. 1978. One molecule of diphtheria toxin fragment A introduced into a cell can kill the cell. *Cell* 15, 245–250.

All publications, patents and patent applications are herein incorporated by reference in their entirety to the same extent as if each individual publication, patent or patent application was specifically and individually indicated to be incorporated by reference in its entirety.

What is claimed is:

1. A method of expressing a heterologous gene in a mammalian liver cell in vitro comprising inserting a DNA construct into a mammalian liver cell, said construct comprising three or more human AFP enhancer regions and a human AFP promoter functionally linked to the heterologous gene in the absence of a AFP silencer region, and expressing the heterologous gene in the mammalian liver cells in vitro.

2. A method of killing cells in vitro which constitutively express AFP comprising inserting a DNA construct into a mammalian cell, said construct comprising a human AFP enhancer region, a human AFP silencer region and a human AFP promoter sequence functionally linked to a direct toxin gene and expressing the toxin gene in the mammalian cells under conditions such that the cells which constitutively express AFP are substantively killed in vitro.

3. The method of claim 2 wherein the construct comprises three or more silencer regions.

4. The method of claim 2 wherein the construct comprises three or more enhancer regions.

\* \* \* \* \*

SEQUENCE LISTING ( 1 ) GENERAL INFORMATION:

( i i i ) NUMBER OF SEQUENCES: 46

( 2 ) INFORMATION FOR SEQ ID NO:1:

( i ) SEQUENCE CHARACTERISTICS:
        ( A ) LENGTH: 13 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:1:

GTCAATTAGT AAC                                       1 3

( 2 ) INFORMATION FOR SEQ ID NO:2:

( i ) SEQUENCE CHARACTERISTICS:
        ( A ) LENGTH: 13 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:2:

GTTAGTAATT ACT                                       1 3

( 2 ) INFORMATION FOR SEQ ID NO:3:

( i ) SEQUENCE CHARACTERISTICS:
        ( A ) LENGTH: 13 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:3:

GTTAATAATC TAC                                       1 3

( 2 ) INFORMATION FOR SEQ ID NO:4:

( i ) SEQUENCE CHARACTERISTICS:
        ( A ) LENGTH: 13 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:4:

GTTAATTATT GGC                                       1 3

( 2 ) INFORMATION FOR SEQ ID NO:5:

( i ) SEQUENCE CHARACTERISTICS:
        ( A ) LENGTH: 13 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:5:

GTTACTAGTT AAC　　　　　　　　　　　　　　　　　　　　　　　　　　　　　　　　　　　　　　　　　　　　13

( 2 ) INFORMATION FOR SEQ ID NO:6:

( i ) SEQUENCE CHARACTERISTICS:
　　　　　　　　( A ) LENGTH: 409 base pairs
　　　　　　　　( B ) TYPE: nucleic acid
　　　　　　　　( C ) STRANDEDNESS: double
　　　　　　　　( D ) TOPOLOGY: linear ( x i ) SEQUENCE DESCRIPTION: SEQ ID NO:6:

| AGCTTATATA | GTTTGCTTCA | TAAAACTCTA | TTTCAGTTCT | TCATAACTAA | TACTTCATGA | 60 |
| CTATTGCTTT | TCAGGTATTC | CTTCATAACA | AATACTTTGG | CTTTCATATA | TTTGAGTAAA | 120 |
| GTCCCCCTTG | AGGAAGAGTA | GAAGAACTGC | ACTTTGTAAA | TACTATCCTG | GAATCCAAAC | 180 |
| GGATAGACAA | GGATGGTGCT | ACCTCTTTCT | GGAGAGTACG | TGAGCAAGGC | CTGTTTTGTT | 240 |
| AACATGTTCC | TTAGGAGACA | AAACTTAGGA | GAGACACGCA | TAGCAGAAAA | TGGACAAAAA | 300 |
| CTAACAAATG | AATGGGAATT | GTACTTGATT | AGCATTGAAG | ACCTTGTTTA | TACTATGATA | 360 |
| AATGTTTGTA | TTTGCTGGAA | GTGCTACTGA | CGGTAAACCC | TTTTTGTTT | | 409 |

( 2 ) INFORMATION FOR SEQ ID NO:7:

( i ) SEQUENCE CHARACTERISTICS:
　　　　　　　　( A ) LENGTH: 234 base pairs
　　　　　　　　( B ) TYPE: nucleic acid
　　　　　　　　( C ) STRANDEDNESS: double
　　　　　　　　( D ) TOPOLOGY: linear ( x i ) SEQUENCE DESCRIPTION: SEQ ID NO:7:

| TGGCATATGA | TAGGCATTTA | ATAGTTTTAA | AGAATTAATG | TATTTAGATG | AATTGCATAC | 60 |
| CAAATCTGCT | GTCTTTTCTT | TATGGCTTCA | TTAACTTAAT | TTGAGAGAAA | TTAATTATTC | 120 |
| TGCAACTTAG | GGACAAGTCA | TCTCTTTGAA | TATTCTGTAG | TTTGAGGAGA | ATATTTGTTA | 180 |
| TATTTGCAAA | ATAAATAAG | TTTGCAAGTT | TTTTTTTCT | GCCCCAAAGA | GCTC | 234 |

( 2 ) INFORMATION FOR SEQ ID NO:8:

( i ) SEQUENCE CHARACTERISTICS:
　　　　　　　　( A ) LENGTH: 39 base pairs
　　　　　　　　( B ) TYPE: nucleic acid
　　　　　　　　( C ) STRANDEDNESS: double
　　　　　　　　( D ) TOPOLOGY: linear ( x i ) SEQUENCE DESCRIPTION: SEQ ID NO:8:

GATCTCAGTT CTTCATAACT AATACTTCAT GACTAGATC　　　　　　　　　　　　　　　　　　　　　　　　　39

( 2 ) INFORMATION FOR SEQ ID NO:9:

( i ) SEQUENCE CHARACTERISTICS:
　　　　　　　　( A ) LENGTH: 39 base pairs
　　　　　　　　( B ) TYPE: nucleic acid
　　　　　　　　( C ) STRANDEDNESS: double
　　　　　　　　( D ) TOPOLOGY: linear ( x i ) SEQUENCE DESCRIPTION: SEQ ID NO:9:

GATCTCAGTT GTTCGTAAGT AATACTTCAT GACTAGATC　　　　　　　　　　　　　　　　　　　　　　　　　39

( 2 ) INFORMATION FOR SEQ ID NO:10:

( i ) SEQUENCE CHARACTERISTICS:
　　　　　　　　( A ) LENGTH: 21 base pairs (B) TYPE: nucleic acid
(C) STRANDEDNESS: double
(D) TOPOLOGY: linear (xi) SEQUENCE DESCRIPTION: SEQ ID NO:10:

AAGCTTAAGC ATATGGGCGC C    21

(2) INFORMATION FOR SEQ ID NO:11:

(i) SEQUENCE CHARACTERISTICS:
(A) LENGTH: 14 base pairs
(B) TYPE: nucleic acid
(C) STRANDEDNESS: double
(D) TOPOLOGY: linear (xi) SEQUENCE DESCRIPTION: SEQ ID NO:11:

TGATAATAGT TATC    14

(2) INFORMATION FOR SEQ ID NO:12:

(i) SEQUENCE CHARACTERISTICS:
(A) LENGTH: 2240 base pairs
(B) TYPE: nucleic acid
(C) STRANDEDNESS: double
(D) TOPOLOGY: linear (xi) SEQUENCE DESCRIPTION: SEQ ID NO:12:

```
GAATTCTTAG AAATATGGGG GTAGGGGTGG TGGTGGTAAT TCTGTTTTCA CCCCATAGGT      60
GAGATAAGCA TTGGGTTAAA TGTGCTTTCA CACACACATC ACATTTCATA AGAATTAAGG     120
AACAGACTAT GGGCTGGAGG ACTTTGAGGA TGTCTGTCTC ATAACACTTG GGTTGTATCT     180
GTTCTATGGG GCTTGTTTTA AGCTTGGCAA CTTGCAACAG GGTTCACTGA CTTTCTCCCC     240
AAGCCCAAGG TACTGTCCTC TTTTCATATC TGTTTTGGGG CCTCTGGGGC TTGAATATCT     300
GAGAAAATAT AAACATTTCA ATAATGTTCT GTGGTGAGAT GAGTATGAGA GATGTGTCAT     360
TCATTTGTAT CAATGAATGA ATGAGGACAA TTAGTGTATA AATCCTTAGT ACAACAATCT     420
GAGGGTAGGG GTGGTACTAT TCAATTTCTA TTTATAAAGA TACTTATTTC TATTTATTTA     480
TGCTTGTGAC AAATGTTTTG TTCGGGACCA CAGGAATCAC AAAGATGAGT CTTTGAATTT     540
AAGAAGTTAA TGGTCCAGGA ATAATTACAT AGCTTACAAA TGACTATGAT ATACCATCAA     600
ACAAGAGGTT CCATGAGAAA ATAATCTGAA AGGTTTAATA AGTTGTCAAA GGTGAGAGGG     660
CTCTTCTCTA GCTAGAGACT AATCAGAAAT ACATTCAGGG ATAATTATTT GAATAGACCT     720
TAAGGGTTGG GTACATTTTG TTCAAGCATT GATGGAGAAG GAGAGTGAAT ATTTGAAAAC     780
ATTTTCAACT AACCAACCAC CCAATCCAAC AAACAAAAAA TGAAAAGAAT CTCAGAAACA     840
GTGAGATAAG AGAAGGAATT TTCTCACAAC CCACACGTAT AGCTCAACTG CTCTGAAGAA     900
GTATATATCT AATATTTAAC ACTAACATCA TGCTAATAAT GATAATAATT ACTGTCATTT     960
TTTAATGTCT ATAAGTACCA GGCATTTAGA AGATATTATT CCATTTATAT ATCAAAATAA    1020
ACTTGAGGGG ATAGATCATT TTCATGATAT ATGAGAAAAA TTAAAAACAG ATTGAATTAT    1080
TTGCCTGTCA TACAGCTAAT AATTGACCAT AAGACAATTA GATTAAATT AGTTTTGAAT    1140
CTTTCTAATA CCAAAGTTCA GTTACTGTT CCATGTTGCT TCTGAGTGGC TTCACAGACT    1200
TATGAAAAAG TAAACGGAAT CAGAATTACA TCAATGCAAA AGCATTGCTG TGAACTCTGT    1260
ACTTAGGACT AAACTTTGAG CAATAACACA CATAGATTGA GGATTGTTTG CTGTTAGCAT    1320
ACAAACTCTG GTTCAAAGCT CCTCTTTATT GCTTGTCTTG GAAAATTTGC TGTTCTTCAT    1380
GGTTTCTCTT TTCACTGCTA TCTATTTTTC TCAACCACTC ACATGGCTAC AATAACTGTC    1440
```

| | | | | | | |
|---|---|---|---|---|---|---|
| TGCAAGCTTA | TGATTCCCAA | ATATCTATCT | CTAGCCTCAA | TCTTGTTCCA | GAAGATAAAA | 1500 |
| AGTAGTATTC | AAATGCACAT | CAACGTCTCC | ACTTGGAGGG | CTTAAAGACG | TTTCAACATA | 1560 |
| CAAACCGGGG | AGTTTTGCCT | GGAATGTTTC | CTAAATGTG | TCCTGTAGCA | CATAGGGTCC | 1620 |
| TCTTGTTCCT | TAAAATCTAA | TTACTTTTAG | CCCAGTGCTC | ATCCACCTA | TGGGGAGATG | 1680 |
| AGAGTGAAAA | GGGAGCCTGA | TTAATAATTA | CACTAAGTCA | ATAGGCATAG | AGCCAGGACT | 1740 |
| GTTTGGGTAA | ACTGGTCACT | TTATCTTAAA | CTAAATATAT | CCAAAACTGA | ACATGTACTT | 1800 |
| AGTTACTAAG | TCTTTGACTT | TATCTCATTC | ATACCACTCA | GCTTATCCA | GGCCACTTAT | 1860 |
| TTGACAGTAT | TATTGCGAAA | ACTTCCTAAC | TGGTCTCCTT | ATCATAGTCT | TATCCCCTTT | 1920 |
| TGAAACAAAA | GAGACAGTTT | CAAAATACAA | ATATGATTTT | TATTAGCTCC | CTTTGTTGT | 1980 |
| CTATAATAGT | CCCAGAAGGA | GTTATAAACT | CCATTTAAAA | AGTCTTTGAG | ATGTGGCCCT | 2040 |
| TGCCAACTTT | GCCAGGAATT | CCCAATATCT | AGTATTTTCT | ACTATTAAAC | TTTGTGCCTC | 2100 |
| TTCAAAACTG | CATTTTCTCT | CATTCCCTAA | GTGTGCATTG | TTTTCCCTTA | CCGGTTGGTT | 2160 |
| TTTCCACCAC | CTTTTACATT | TTCCTGGAAC | ACTATACCCT | CCCTCTTCAT | TTGGCCCACC | 2220 |
| TCTAATTTTC | TTTCAGATCT | | | | | 2240 |

( 2 ) INFORMATION FOR SEQ ID NO:13:

( i ) SEQUENCE CHARACTERISTICS:
        ( A ) LENGTH: 13 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:13:

GTTAAGTATT GGC        13

( 2 ) INFORMATION FOR SEQ ID NO:14:

( i ) SEQUENCE CHARACTERISTICS:
        ( A ) LENGTH: 13 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:14:

GTTACGAGTT AAC        13

( 2 ) INFORMATION FOR SEQ ID NO:15:

( i ) SEQUENCE CHARACTERISTICS:
        ( A ) LENGTH: 41 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:15:

AATTCTTTCT AATACCAAAG TTCAGTTTAC TGTTCCAGAT C        41

( 2 ) INFORMATION FOR SEQ ID NO:16:

( i ) SEQUENCE CHARACTERISTICS:
        ( A ) LENGTH: 41 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:16:

AATTCTTTCT AATACCGACG CTCCGTTTAC TGTTCCAGAT C        41

( 2 ) INFORMATION FOR SEQ ID NO:17:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:17:

GATCAGAATT ACATCAATGC AAAGATC 27

( 2 ) INFORMATION FOR SEQ ID NO:18:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:18:

GATCACAATT ACGTCAACGC AAAGATC 27

( 2 ) INFORMATION FOR SEQ ID NO:19:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:19:

GATCTTGTTT GCTGTTAGCA TACAAACTCG ATC 33

( 2 ) INFORMATION FOR SEQ ID NO:20:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:20:

GATCTAGCTT GCTGTTAGCA TACCAGCTCG ATC 33

( 2 ) INFORMATION FOR SEQ ID NO:21:

( i ) SEQUENCE CHARACTERISTICS:
        ( A ) LENGTH: 38 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:21:

GATCTATTTT TCTCAACCAC TCACATGGCT ACAAGATC 38

( 2 ) INFORMATION FOR SEQ ID NO:22:

( i ) SEQUENCE CHARACTERISTICS:
        ( A ) LENGTH: 38 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:22:

GATCTATTTT TCTCAACTAC CCACATGGCT ACAAGATC 38

( 2 ) INFORMATION FOR SEQ ID NO:23:

( i ) SEQUENCE CHARACTERISTICS:
  ( A ) LENGTH: 33 base pairs
  ( B ) TYPE: nucleic acid
  ( C ) STRANDEDNESS: double
  ( D ) TOPOLOGY: linear ( x i ) SEQUENCE DESCRIPTION: SEQ ID NO:23:

GATCCTGATT AATAATTACA CTAAGTCAAG ATC   33

( 2 ) INFORMATION FOR SEQ ID NO:24:

( i ) SEQUENCE CHARACTERISTICS:
  ( A ) LENGTH: 33 base pairs
  ( B ) TYPE: nucleic acid
  ( C ) STRANDEDNESS: double
  ( D ) TOPOLOGY: linear ( x i ) SEQUENCE DESCRIPTION: SEQ ID NO:24:

GATCCTGATT AATAAGTACA CTAAGTCAAG ATC   33

( 2 ) INFORMATION FOR SEQ ID NO:25:

( i ) SEQUENCE CHARACTERISTICS:
  ( A ) LENGTH: 39 base pairs
  ( B ) TYPE: nucleic acid
  ( C ) STRANDEDNESS: double
  ( D ) TOPOLOGY: linear ( x i ) SEQUENCE DESCRIPTION: SEQ ID NO:25:

GATCTCAGTT GTTCGTAACT AAGACTTCAT GACTAGATC   39

( 2 ) INFORMATION FOR SEQ ID NO:26:

( i ) SEQUENCE CHARACTERISTICS:
  ( A ) LENGTH: 582 base pairs
  ( B ) TYPE: nucleic acid
  ( C ) STRANDEDNESS: double
  ( D ) TOPOLOGY: linear ( i x ) FEATURE:
  ( A ) NAME/KEY: CDS
  ( B ) LOCATION: 1..582

( x i ) SEQUENCE DESCRIPTION: SEQ ID NO:26:

```
GCA  GGC  GCT  GAT  GAT  GTT  GTT  GAT  TCT  TCT  AAA  TCT  TTT  GTG  ATG  GAA      48
Ala  Gly  Ala  Asp  Asp  Val  Val  Asp  Ser  Ser  Lys  Ser  Phe  Val  Met  Glu
 1             5                        10                       15

AAC  TTT  TCT  TCG  TAC  CAC  GGG  ACT  AAA  CCT  GGT  TAT  GTA  GAT  TCC  ATT      96
Asn  Phe  Ser  Ser  Tyr  His  Gly  Thr  Lys  Pro  Gly  Tyr  Val  Asp  Ser  Ile
                    20                   25                       30

CAA  AAA  GGT  ATA  CAA  AAG  CCA  AAA  TCT  GGT  ACA  CAA  GGA  AAT  TAT  GAC     144
Gln  Lys  Gly  Ile  Gln  Lys  Pro  Lys  Ser  Gly  Thr  Gln  Gly  Asn  Tyr  Asp
               35                        40                       45

GAT  GAT  TGG  AAA  GGG  TTT  TAT  AGT  ACC  GAC  AAT  AAA  TAC  GAC  GCT  GCG     192
Asp  Asp  Trp  Lys  Gly  Phe  Tyr  Ser  Thr  Asp  Asn  Lys  Tyr  Asp  Ala  Ala
          50                        55                   60

GGA  TAC  TCT  GTA  GAT  AAT  GAA  AAC  CCG  CTC  TCT  GGA  AAA  GCT  GGA  GGC     240
Gly  Tyr  Ser  Val  Asp  Asn  Glu  Asn  Pro  Leu  Ser  Gly  Lys  Ala  Gly  Gly
 65                        70                   75                          80

GTG  GTC  AAA  GTG  ACG  TAT  CCA  GGA  CTG  ACG  AAG  GTT  CTC  GCA  CTA  AAA     288
Val  Val  Lys  Val  Thr  Tyr  Pro  Gly  Leu  Thr  Lys  Val  Leu  Ala  Leu  Lys
                    85                        90                       95

GTG  GAT  AAT  GCC  GAA  ACT  ATT  AAG  AAA  GAG  TTA  GGT  TTA  AGT  CTC  ACT     336
Val  Asp  Asn  Ala  Glu  Thr  Ile  Lys  Lys  Glu  Leu  Gly  Leu  Ser  Leu  Thr
                    100                  105                      110
```

| | | | | | | | | | | | | | | | | |
|---|---|---|---|---|---|---|---|---|---|---|---|---|---|---|---|---|
| GAA | CCG | TTG | ATG | GAG | CAA | GTC | GGA | ACG | GAA | GAG | TTT | ATC | AAA | AGG | TTC | 384 |
| Glu | Pro | Leu | Met | Glu | Gln | Val | Gly | Thr | Glu | Glu | Phe | Ile | Lys | Arg | Phe | |
| | 115 | | | | | 120 | | | | | | 125 | | | | |
| GGT | GAT | GGT | GCT | TCG | CGT | GTA | GTG | CTC | AGC | CTT | CCC | TTC | GCT | GAG | GGG | 432 |
| Gly | Asp | Gly | Ala | Ser | Arg | Val | Val | Leu | Ser | Leu | Pro | Phe | Ala | Glu | Gly | |
| 130 | | | | | | 135 | | | | | | 140 | | | | |
| AGT | TCT | AGC | GTT | GAA | TAT | ATT | AAT | AAC | TGG | GAA | CAG | GCG | AAA | GCG | TTA | 480 |
| Ser | Ser | Ser | Val | Glu | Tyr | Ile | Asn | Asn | Trp | Glu | Gln | Ala | Lys | Ala | Leu | |
| 145 | | | | | 150 | | | | | 155 | | | | | 160 | |
| AGC | GTA | GAA | CTT | GAG | ATT | AAT | TTT | GAA | ACC | CGT | GGA | AAA | CGT | GGC | CAA | 528 |
| Ser | Val | Glu | Leu | Glu | Ile | Asn | Phe | Glu | Thr | Arg | Gly | Lys | Arg | Gly | Gln | |
| | | | | 165 | | | | | 170 | | | | | 175 | | |
| GAT | GCG | ATG | TAT | GAG | TAT | ATG | GCT | CAA | GCC | TGT | GCA | GGA | AAT | CGT | GTC | 576 |
| Asp | Ala | Met | Tyr | Glu | Tyr | Met | Ala | Gln | Ala | Cys | Ala | Gly | Asn | Arg | Val | |
| | | 180 | | | | | 185 | | | | | 190 | | | | |
| AGG | CGA | | | | | | | | | | | | | | | 582 |
| Arg | Arg | | | | | | | | | | | | | | | |

(2) INFORMATION FOR SEQ ID NO:27:

(i) SEQUENCE CHARACTERISTICS:
        (A) LENGTH: 194 amino acids
        (B) TYPE: amino acid
        (D) TOPOLOGY: linear (ii) MOLECULE TYPE: protein (xi) SEQUENCE DESCRIPTION: SEQ ID NO:27:

| | | | | | | | | | | | | | | |
|---|---|---|---|---|---|---|---|---|---|---|---|---|---|---|
| Ala | Gly | Ala | Asp | Asp | Val | Val | Asp | Ser | Ser | Lys | Ser | Phe | Val | Met | Glu |
| 1 | | | | 5 | | | | | 10 | | | | | 15 | |
| Asn | Phe | Ser | Ser | Tyr | His | Gly | Thr | Lys | Pro | Gly | Tyr | Val | Asp | Ser | Ile |
| | | | 20 | | | | | 25 | | | | | 30 | | |
| Gln | Lys | Gly | Ile | Gln | Lys | Pro | Lys | Ser | Gly | Thr | Gln | Gly | Asn | Tyr | Asp |
| | | | 35 | | | | | 40 | | | | | 45 | | |
| Asp | Asp | Trp | Lys | Gly | Phe | Tyr | Ser | Thr | Asp | Asn | Lys | Tyr | Asp | Ala | Ala |
| | 50 | | | | | 55 | | | | | 60 | | | | |
| Gly | Tyr | Ser | Val | Asp | Asn | Glu | Asn | Pro | Leu | Ser | Gly | Lys | Ala | Gly | Gly |
| 65 | | | | | 70 | | | | | 75 | | | | | 80 |
| Val | Val | Lys | Val | Thr | Tyr | Pro | Gly | Leu | Thr | Lys | Val | Leu | Ala | Leu | Lys |
| | | | | 85 | | | | | 90 | | | | | 95 | |
| Val | Asp | Asn | Ala | Glu | Thr | Ile | Lys | Lys | Glu | Leu | Gly | Leu | Ser | Leu | Thr |
| | | | 100 | | | | | 105 | | | | | 110 | | |
| Glu | Pro | Leu | Met | Glu | Gln | Val | Gly | Thr | Glu | Glu | Phe | Ile | Lys | Arg | Phe |
| | | 115 | | | | | 120 | | | | | 125 | | | |
| Gly | Asp | Gly | Ala | Ser | Arg | Val | Val | Leu | Ser | Leu | Pro | Phe | Ala | Glu | Gly |
| | 130 | | | | | 135 | | | | | 140 | | | | |
| Ser | Ser | Ser | Val | Glu | Tyr | Ile | Asn | Asn | Trp | Glu | Gln | Ala | Lys | Ala | Leu |
| 145 | | | | | 150 | | | | | 155 | | | | | 160 |
| Ser | Val | Glu | Leu | Glu | Ile | Asn | Phe | Glu | Thr | Arg | Gly | Lys | Arg | Gly | Gln |
| | | | | 165 | | | | | 170 | | | | | 175 | |
| Asp | Ala | Met | Tyr | Glu | Tyr | Met | Ala | Gln | Ala | Cys | Ala | Gly | Asn | Arg | Val |
| | | 180 | | | | | 185 | | | | | 190 | | | |
| Arg | Arg | | | | | | | | | | | | | | |

(2) INFORMATION FOR SEQ ID NO:28:

(i) SEQUENCE CHARACTERISTICS:
        (A) LENGTH: 585 base pairs
        (B) TYPE: nucleic acid
        (C) STRANDEDNESS: double -continued ( D ) TOPOLOGY: linear ( i x ) FEATURE:
    ( A ) NAME/KEY: CDS
    ( B ) LOCATION: 1..585

( x i ) SEQUENCE DESCRIPTION: SEQ ID NO:28:

```
ATG GGC GCC GAT GAT GTT GTT GAT TCT TCT AAA TCT TTT GTG ATG GAA    48
Met Gly Ala Asp Asp Val Val Asp Ser Ser Lys Ser Phe Val Met Glu
 1               5                  10                  15

AAC TTT TCT TCG TAC CAC GGG ACT AAA CCT GGT TAT GTA GAT TCC ATT    96
Asn Phe Ser Ser Tyr His Gly Thr Lys Pro Gly Tyr Val Asp Ser Ile
                 20                  25                  30

CAA AAA GGT ATA CAA AAG CCA AAA TCT GGT ACA CAA GGA AAT TAT GAC   144
Gln Lys Gly Ile Gln Lys Pro Lys Ser Gly Thr Gln Gly Asn Tyr Asp
             35                  40                  45

GAT GAT TGG AAA GGG TTT TAT AGT ACC GAC AAT AAA TAC GAC GCT GCG   192
Asp Asp Trp Lys Gly Phe Tyr Ser Thr Asp Asn Lys Tyr Asp Ala Ala
         50                  55                  60

GGA TGC TCT GTA GAT AAT GAA AAC CCG CTC TCT GGA AAA GCT GGA GGC   240
Gly Cys Ser Val Asp Asn Glu Asn Pro Leu Ser Gly Lys Ala Gly Gly
 65                  70                  75                  80

GTG GTC AAA GTG ACG TAT CCA GGG CTG ACG AAG GTT CTC GCA CTA AAA   288
Val Val Lys Val Thr Tyr Pro Gly Leu Thr Lys Val Leu Ala Leu Lys
                 85                  90                  95

GTG GAT AAT GCC GAA ACT ATT AAG AAA GAG TTA GGT TTA AGT CTC ACT   336
Val Asp Asn Ala Glu Thr Ile Lys Lys Glu Leu Gly Leu Ser Leu Thr
            100                 105                 110

GAA CCG TTG ATG GAG CAA GTC GGA ACG GAA GAG TTT ATC AAA AGG TTC   384
Glu Pro Leu Met Glu Gln Val Gly Thr Glu Glu Phe Ile Lys Arg Phe
            115                 120                 125

GGT GAT GGT GCT TCG CGT GTA GTG CTC AGC CTT CCC TTC GCT GAG GGG   432
Gly Asp Gly Ala Ser Arg Val Val Leu Ser Leu Pro Phe Ala Glu Gly
        130                 135                 140

AGT TCT AGC GTT GAA TAT ATT AAT AAC TGG GAA CAG GCG AAA GCG TTA   480
Ser Ser Ser Val Glu Tyr Ile Asn Asn Trp Glu Gln Ala Lys Ala Leu
145                 150                 155                 160

AGC GTA GAA CTT GAG ATT AAT TTT GAA ACC CGT GGA AAA CGT GGC CAA   528
Ser Val Glu Leu Glu Ile Asn Phe Glu Thr Arg Gly Lys Arg Gly Gln
                165                 170                 175

GAT GCG ATG TAT GAG TAT ATG GCG CAA GCC TGC GCA GGT AAC CGT GTC   576
Asp Ala Met Tyr Glu Tyr Met Ala Gln Ala Cys Ala Gly Asn Arg Val
            180                 185                 190

AGG CCA TGA                                                       585
Arg Pro
        195
```

( 2 ) INFORMATION FOR SEQ ID NO:29:

( i ) SEQUENCE CHARACTERISTICS:
        ( A ) LENGTH: 194 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

```
Met Gly Ala Asp Asp Val Val Asp Ser Ser Lys Ser Phe Val Met Glu
 1               5                  10                  15

Asn Phe Ser Ser Tyr His Gly Thr Lys Pro Gly Tyr Val Asp Ser Ile
                 20                  25                  30

Gln Lys Gly Ile Gln Lys Pro Lys Ser Gly Thr Gln Gly Asn Tyr Asp
             35                  40                  45
```

Asp Asp Trp Lys Gly Phe Tyr Ser Thr Asp Asn Lys Tyr Asp Ala Ala
            50                      55                  60

Gly Cys Ser Val Asp Asn Glu Asn Pro Leu Ser Gly Lys Ala Gly Gly
 65                  70                  75                  80

Val Val Lys Val Thr Tyr Pro Gly Leu Thr Lys Val Leu Ala Leu Lys
                 85                  90                  95

Val Asp Asn Ala Glu Thr Ile Lys Lys Glu Leu Gly Leu Ser Leu Thr
            100                     105                 110

Glu Pro Leu Met Glu Gln Val Gly Thr Glu Glu Phe Ile Lys Arg Phe
        115                     120                 125

Gly Asp Gly Ala Ser Arg Val Val Leu Ser Leu Pro Phe Ala Glu Gly
    130                     135                 140

Ser Ser Ser Val Glu Tyr Ile Asn Asn Trp Glu Gln Ala Lys Ala Leu
145                 150                     155                 160

Ser Val Glu Leu Glu Ile Asn Phe Glu Thr Arg Gly Lys Arg Gly Gln
                165                     170                 175

Asp Ala Met Tyr Glu Tyr Met Ala Gln Ala Cys Ala Gly Asn Arg Val
            180                     185                 190

Arg Pro ( 2 ) INFORMATION FOR SEQ ID NO:30:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

CAACGGTGGT ATATCCAGTG 20

( 2 ) INFORMATION FOR SEQ ID NO:31:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

AGTCATGCCC GCTTTTGAGA 20

( 2 ) INFORMATION FOR SEQ ID NO:32:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

GTGATAGTAG CCTTGTCCTC 20

( 2 ) INFORMATION FOR SEQ ID NO:33:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

ATGCTGTGAA TTATTG                                                                    16

(2) INFORMATION FOR SEQ ID NO:34:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:34:

CTGTTAAGTA TTGGCA                                                                    16

(2) INFORMATION FOR SEQ ID NO:35:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:35:

TTAATTATGG GCAAAT                                                                    16

(2) INFORMATION FOR SEQ ID NO:36:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:36:

ATTATTGGAA AATGTC                                                                    16

(2) INFORMATION FOR SEQ ID NO:37:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:37:

CAAAAGGTGA CTAGTT                                                                    16

(2) INFORMATION FOR SEQ ID NO:38:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:38:

AGGTTACGAG TTAACA                                                                    16

(2) INFORMATION FOR SEQ ID NO:39:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:39:

TTACTAGTGA ACAGGC                                                                    16

( 2 ) INFORMATION FOR SEQ ID NO:40:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

CTAGTTAAAA GGCATT       16

( 2 ) INFORMATION FOR SEQ ID NO:41:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

GATCAGATCT TACAAATAAC CGCTATGCTG       30

( 2 ) INFORMATION FOR SEQ ID NO:42:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

GATCAGATCT TTTCAACCTA AGGAAATACC       30

( 2 ) INFORMATION FOR SEQ ID NO:43:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

CGAGGTCGAC GGTATCG       17

( 2 ) INFORMATION FOR SEQ ID NO:44:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

TCTAGAACTA GTGGATC       17

( 2 ) INFORMATION FOR SEQ ID NO:45:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:45:

ATTAACCCTC ACTAAAG       17

( 2 ) INFORMATION FOR SEQ ID NO:46:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:46:

```
TAATACGACT CACTATAGGG                                           20
```